(12) United States Patent
Balakrishnan et al.

(10) Patent No.: US 10,172,540 B2
(45) Date of Patent: *Jan. 8, 2019

(54) MULTI-ACTIVITY PLATFORM AND INTERFACE

(71) Applicant: NIKE, Inc., Beaverton, OR (US)

(72) Inventors: Ashok Balakrishnan, Portland, OR (US); Christopher W. Davis, Portland, OR (US); Jefferson Lyman, Portland, OR (US); Sridhar Setti, Beaverton, OR (US); Wade Convay, New York, NY (US); Tara Greer, New York, NY (US); Gaurabh Mathure, New York, NY (US); Christopher C. Thorwarth, Glen Rock, NJ (US)

(73) Assignee: NIKE, Inc., Beaverton, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/072,058

(22) Filed: Mar. 16, 2016

(65) Prior Publication Data

US 2016/0296798 A1    Oct. 13, 2016

Related U.S. Application Data

(63) Continuation of application No. 13/744,988, filed on Jan. 18, 2013, now Pat. No. 9,323,868.

(Continued)

(51) Int. Cl.
*A61B 5/00*    (2006.01)
*A61B 5/11*    (2006.01)
(Continued)

(52) U.S. Cl.
CPC ........... *A61B 5/1118* (2013.01); *A61B 5/1112* (2013.01); *G06F 17/40* (2013.01);
(Continued)

(58) Field of Classification Search
CPC . A63B 24/00; A63B 24/0059; A63B 24/0062; A63B 24/0084; G06F 17/30575;
(Continued)

(56) References Cited

U.S. PATENT DOCUMENTS 6,085,248 A    7/2000  Sambamurthy et al.
7,670,263 B2   3/2010  Ellis et al.
(Continued)

FOREIGN PATENT DOCUMENTS

CN    101978374 A    2/2011
EP       700661 A2    3/1996
(Continued)

OTHER PUBLICATIONS

Jun. 10, 2013—(WO) International Search Report and Written Opinion—App. PCT/US2003/022180.
(Continued)

*Primary Examiner* — Jennifer M Deichl
(74) *Attorney, Agent, or Firm* — Banner & Witcoff, Ltd.

(57) ABSTRACT

A multi-activity system may be configured to receive, upload, synchronize and process data for a variety of different activity types and/or recorded using multiple types of activity monitoring devices. In one example, an application interface may be defined with a multiple functions that are each useable by various types of devices and for processing multiple types of data. Additionally or alternatively, data for different activity types and/or recorded using different types of monitoring devices may be processed differently. Synchronization of data may further be handled on a device-by-device basis, device-type basis and/or activity-type basis using various tracking parameters.

20 Claims, 43 Drawing Sheets

Related U.S. Application Data

(60) Provisional application No. 61/588,610, filed on Jan. 19, 2012.

(51) Int. Cl.
  *G06F 17/40* (2006.01)
  *G16H 15/00* (2018.01)
  *H04L 29/08* (2006.01)
  *G06F 19/00* (2018.01)

(52) U.S. Cl.
  CPC ......... *G06F 19/3481* (2013.01); *G16H 15/00* (2018.01); *H04L 67/1095* (2013.01); *H04L 67/12* (2013.01); *A61B 5/4866* (2013.01); *A61B 5/681* (2013.01); *A61B 5/7435* (2013.01); *A61B 2503/10* (2013.01); *F04C 2270/0421* (2013.01)

(58) Field of Classification Search
  CPC ......... G06F 17/30174; G06F 17/30578; G06F 17/30581
  See application file for complete search history.

(56) References Cited

U.S. PATENT DOCUMENTS

| | | | |
|---|---|---|---|
| 8,088,044 | B2 | 1/2012 | Tchao et al. |
| 8,162,804 | B2* | 4/2012 | Tagliabue ............ A63B 24/0084 482/8 |
| 2004/0102683 | A1* | 5/2004 | Khanuja ............... A61B 5/0002 600/300 |
| 2004/0133081 | A1 | 7/2004 | Teller et al. |
| 2008/0012701 | A1 | 1/2008 | Kass et al. |
| 2008/0153670 | A1* | 6/2008 | McKirdy ............ A63B 24/0059 482/1 |
| 2008/0176655 | A1 | 7/2008 | James et al. |
| 2008/0200312 | A1 | 8/2008 | Tagliabue |
| 2009/0043531 | A1 | 2/2009 | Kahn et al. |
| 2010/0048358 | A1* | 2/2010 | Tchao ................. G06F 19/3418 482/9 |
| 2011/0003665 | A1* | 1/2011 | Burton ................... G04F 10/00 482/9 |

FOREIGN PATENT DOCUMENTS

| | | |
|---|---|---|
| EP | 2253355 A2 | 11/2010 |
| JP | H08126632 A | 5/1996 |
| JP | 2006218246 A | 8/2006 |
| JP | 2009082430 A | 4/2009 |
| JP | 2009544075 A | 12/2009 |
| JP | 2011508615 A | 3/2011 |
| WO | 0116855 A2 | 3/2001 |
| WO | 2006053000 A2 | 5/2006 |
| WO | 2011028383 A1 | 3/2011 |
| WO | 2011028386 A1 | 3/2011 |
| WO | 2011137678 A1 | 11/2011 |

OTHER PUBLICATIONS

Garmin, "Forefunmer 405CX owner's manual", Internet Citation, Mar. 1, 2009, pp. 1-55, XP002587382.

Jan. 4, 2017—(EP) ESR—App. No. 13703201.7.

Mokey, Nick: "Nike+SportWatch GPS Review", Internet Citation, Apr. 11, 2011 (Apr. 11, 2011), pp. 1-9, XP002751864, Retrieved from the Internet: URL:http://www.digitaltrends.com/fitness-apparel-reviews/nike-plus-sportwatch-gps-review/ [retrieved on Dec. 7, 2015] the whole document.

* cited by examiner

MULTI-ACTIVITY PLATFORM AND INTERFACE

CROSS-REFERENCE TO RELATED APPLICATION

This application is a continuation application of U.S. patent application Ser. No. 13/744,988, entitled "MULTI-ACTIVITY PLATFORM AND INTERFACE," and filed Jan. 18, 2013, which claims priority to U.S. Provisional Application Ser. No. 61/588,610, entitled "MULTI-ACTIVITY PLATFORM AND INTERFACE," and filed on Jan. 19, 2012. The contents of the aforementioned applications are hereby incorporated by reference in their entirety.

BACKGROUND

Exercise and fitness have become increasingly popular and the benefits from such activities are well known. Various types of technology have been incorporated into fitness and other athletic activities. For example, a wide variety of portable electronic devices are available for use in fitness activities, such as MP3 or other audio players, radios, portable televisions, DVD players, or other video playing devices, watches, GPS systems, pedometers, mobile telephones, pagers, beepers, etc. Many fitness enthusiasts or athletes use one or more of these devices when exercising or training to keep them entertained, record and provide performance data or to keep them in contact with others, etc.

BRIEF SUMMARY

The following presents a general summary of aspects of the disclosure in order to provide a basic understanding of at least some of its aspects. This summary is not an extensive overview. It is not intended to identify key or critical elements or to delineate the scope. The following summary merely presents some concepts of the invention in a general form as a prelude to the more detailed description provided below.

Aspects described herein provide activity data recording, on-line communities and interfaces between activity monitoring and tracking devices and systems supporting multiple different types of activities. Additionally or alternatively, the various aspects described herein provide for distinguishing activity data and information based on a type of device through which the activity data was recorded. Still further, activity data from multiple types of activity types, devices and device types and activity sessions may be aggregated toward a single goal. In this manner, goals providing motivation to perform activities (including fitness programs, sports, and other types of physical activity and athletic activity) might no longer limit users to a single activity or device for a particular goal.

Other aspects and features are described throughout the disclosure.

BRIEF DESCRIPTION OF THE DRAWINGS

The present disclosure is illustrated by way of example and not limited in the accompanying figures in which like reference numerals indicate similar elements and in which.

DETAILED DESCRIPTION

In the following description of various example embodiments, reference is made to the accompanying drawings, which form a part hereof, and in which are shown by way of illustration various example devices, systems, and environments in which aspects may be practiced. It is to be understood that other specific arrangements of parts, example devices, systems, and environments may be utilized and structural and functional modifications may be made without departing from the scope of the present disclosure.

Overview

Figure 1:
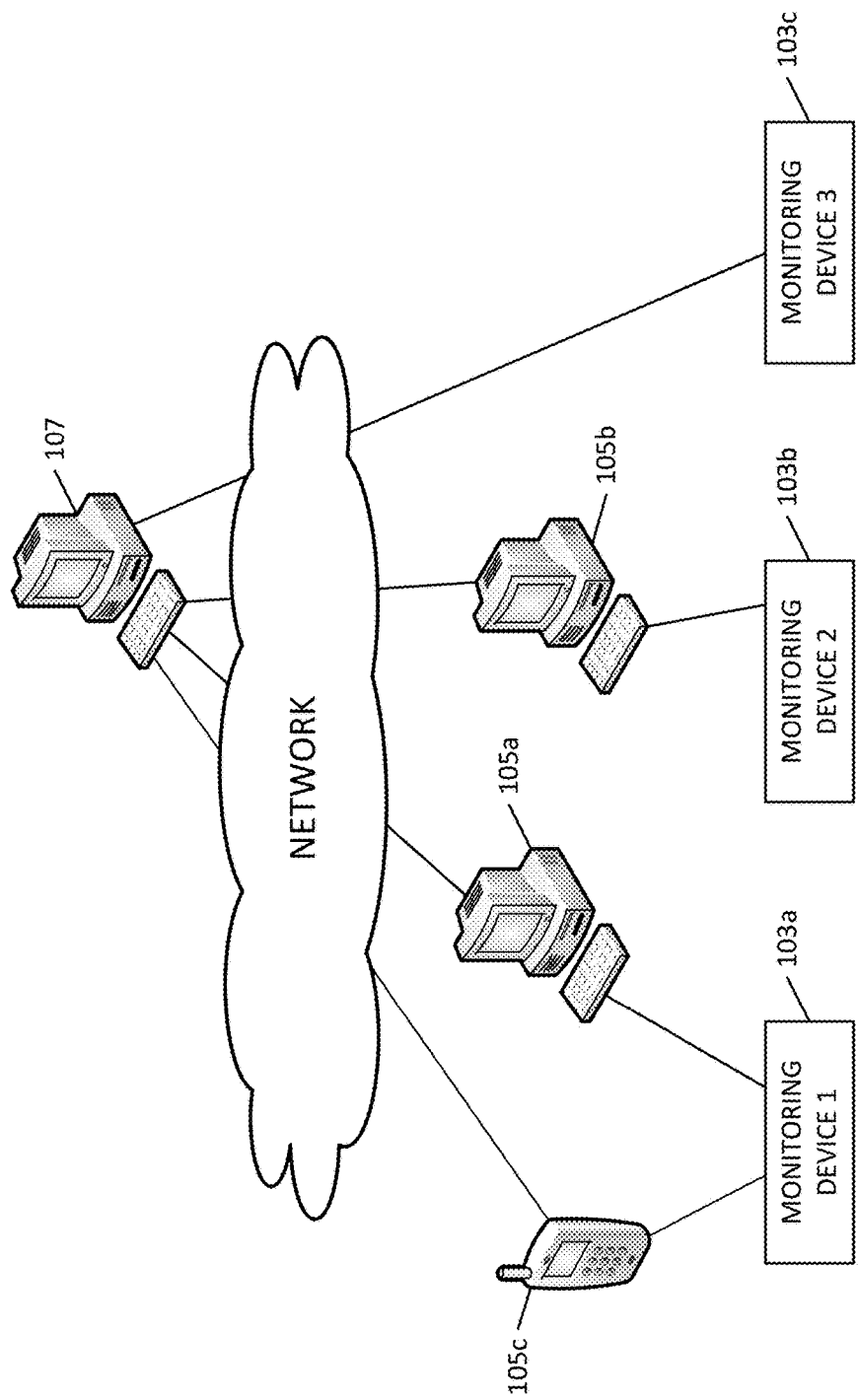
FIG. 1 illustrates an example system in which various features discussed herein may be included and/or implemented.

FIG. 1 illustrates a general network and system environment in which one or more aspects described herein may be used and operate. For example, environment 100 may include multiple devices connected via various types of networks, connections and protocols including the Internet, short-range and long-range wireless communications, wired communications, cellular communications, BLUETOOTH (e.g., Low-Energy), ZIGBEE, RFID, Wi-Fi, WLAN, USB, FireWire and the like and/or combinations thereof. For example, activity monitoring devices 103a and 103b may be connected to computing devices 105a and 105b, respectively, through short-range connections including wired and wireless connections. Activity monitoring device 103c, on the other hand, may be connected to a remote activity monitoring and tracking system 107 via long-range wireless or wired communications including Wi-Fi, cellular communications, TCP/IP, Ethernet and the like and/or combinations thereof.

Activity monitoring devices 103a, 103b and 103c may include any type of activity monitoring system including smartphones, dedicated activity monitoring devices, sensors and the like and/or combinations thereof. Examples of activity monitoring devices are described in: U.S. application Ser. No. 13/287,047, entitled "Wearable Device Having Athletic Functionality," filed Nov. 1, 2011; U.S. patent application Ser. No. 12/767,288 entitled "Athletic Watch," filed Apr. 26, 2010; U.S. patent application Ser. No. 12/767,447 entitled "GPS Features And Functionality In An Athletic Watch System," filed Apr. 26, 2010; U.S. patent application Ser. No. 12/767,425 entitled "Athletic Watch," filed Apr. 26, 2010; U.S. application Ser. No. 12/767,308, entitled "Athletic Watch," filed Apr. 26, 2010; and U.S. application Ser. No. 13/343,587, entitled "Athletic Watch," filed Jan. 4, 2012, the contents of which are hereby incorporated by reference in their entirety.

Activity monitoring devices 103a, 103b, 103c may include different sensors (e.g., heart rate monitor, accelerometer, global positioning system, cellular triangulation system, shock sensors, temperature gauges, gyroscopes, light sensors, etc.), may use different communication or data recording protocols, have different calibrations and/or be configured to detect different types of activity and movement. For example, device 103a may be configured to detect a number of steps and a corresponding pace based thereon while device 103b may be configured to detect heart rate and hip movement (e.g., for basketball or other types of sports). Accordingly, the data recorded by devices 103a and 103b might not be immediately compatible or comparable (e.g., use of differing data recordation protocols). A user may, for instance, have to view metrics and the recorded data using different applications, services or systems so that the information is appropriately processed and visualized or otherwise conveyed. Even between devices having similar components (e.g., devices 103a and 103c), the devices may have different sensitivities or calibrations and thus, the resulting data may still offer inaccurate comparisons of performance.

To facilitate comparisons and to streamline tracking of overall physical activity, activity data may be processed using a multi-activity system and platform such as system 107. System 107 may host an activity monitoring and tracking site and community through which users may track their own activity progress as well as connect with other users to share and/or compare activity levels, compete, engage in joint activities, communicate and the like. As described herein, communication of activity data between monitoring devices 103a and 103b may be facilitated through computing devices 105a and 105b, respectively. Activity monitoring device 103a may further communicate data with device 105c. However, use of computing devices 105a, 105b, and 105c might not be necessary, if, for instance, devices 103a and 103b include communication means (e.g., Internet access or wide-area network access) for interfacing with system 107. In some examples, devices 105a, 105b and 105c may also provide intermediate processing of activity data and include one or more of a multi-activity system and platform's functions and/or capabilities.

System 107 may be configured to provide a single source through which a user may view activity data for a variety of activities and types of activities performed. Rather than having to view basketball activity data, for example, through a first site or system and running data through another site or system, the user may view the information in aggregate through a single platform or system. Additionally, data recorded using different monitoring devices or types of activity monitoring devices such as devices 103a, 103b and 103c may also be aggregated and viewed together. System 107 may also provide visualizations and data processing that allows more granular control of the recorded data and activities. For example, system 107 may provide the user with the ability to view sets of activity data based on the monitoring device used, type of activity monitoring device, type of activity performed, time period, and/or activity session. Moreover, the aggregation of physical activity data by system 107 may allow a user to measure, view and evaluate his or her overall physical activity levels. For example, various physical activity data (e.g., metrics) may be used to determine a virtual activity metric, such as activity points, to provide a basis of comparison between different activities and activity sessions. Additionally, a user may define goals that may be achieved through performing multiple types of activities, even if the multiple types of activities are measured using different metrics or provide different types of sensor data, and/or if the user uses different monitoring devices or types of monitoring devices such as devices 103a, 103b and 103c.

Computing devices 105a, 105b and 105c may be configured to provide data processing similar to that of system 107, without requiring data to be sent to system 107. For example, computing device 105a may receive data from multiple monitoring devices 103a, 103b and/or 103c and provide comparisons and data tracking similar to system 107. Alternatively or additionally, computing devices 105a, 105b and 105c may also be used in some arrangements to provide intermediate storage of data and to facilitate data communication with system 107. For example, if devices 103a and 103b include relatively small memory capacities, computing devices 105a, 105b and 105c may be used to store recorded data from devices 103a and 103b, respectively so that devices 103a and 103b may delete previously recorded activity data to make space to store additional new data. Computing devices 105a, 105b and 105c may correspond to other activity monitoring devices, telecommunication devices such as cellular phones, satellite phones, Internet telephony devices, smart phones and the like, portable computing devices including music players, video players, laptop computers and the like and/or desktop computing systems such as personal computers (PCs).

In one or more arrangements, one or more of devices 105a, 105b and 105c may be configured differently than the other devices. In one example, device 105c may be configured for local synchronization and storage of activity data while one or more of devices 105a and 105b may be configured for pass-through synchronization. Accordingly, activity data may be synchronized between activity monitoring device 103a and device 105c such that activity data is stored on device 105c. The activity data may then be synchronized to multi-activity system 107 at some point in the future. When in pass-through synchronization mode, device 105a may facilitate synchronization between device 103a and multi-activity system 107 without intermediate storage. That is, device 105a might not support synchronization between just device 105a and activity monitoring device 103a. The various synchronization configurations of devices 105a, 105b and 105c may depend on the type of synchronization applications installed and/or executing thereon.

Figure 2:
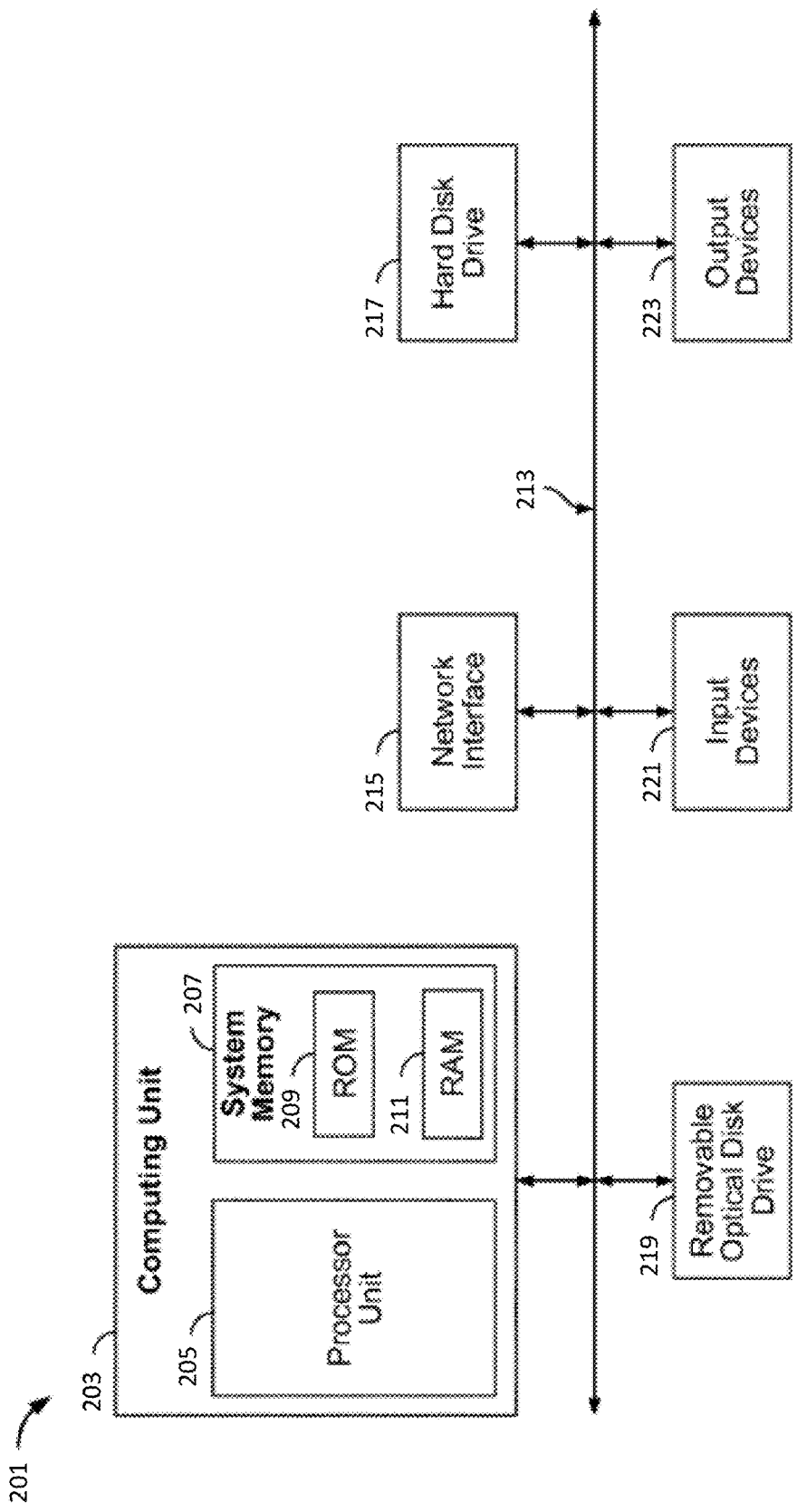
FIG. 2 illustrates an example device in which various features discussed herein may be included and/or implemented.

FIG. 2 illustrates an example computing system that may be included in one or more of the devices described in FIG. 1. For example, computing system 201 may be adapted to operate as any one of devices 103a, 103b, 103c, 105a, 105b and 107. As seen in this figure, the computer 201 has a computing unit 203. The computing unit 203 may include a processing unit 205 and system memory 207. The processing unit 205 may be any type of processing device for executing software instructions, but may conventionally be a microprocessor device. The system memory 207 may include both a read-only memory (ROM) 209 and a random access memory (RAM) 211. As will be appreciated by those of ordinary skill in the art, both the read-only memory (ROM) 209 and the random access memory (RAM) 211 may store software instructions for execution by the processing unit 205.

The processing unit 205 and the system memory 207 are connected, either directly or indirectly, through a bus 213 or alternate communication structure to one or more peripheral devices. For example, the processing unit 205 or the system memory 207 may be directly or indirectly connected to additional memory storage, such as the hard disk drive 217 and the removable optical disk drive 219. Computer 201 may further use or interface with other memory storage mediums such as solid state drives, removable magnetic disk drives and flash memory cards. The processing unit 205 and the system memory 207 also may be directly or indirectly connected to one or more input devices 221 and one or more output devices 223. The input devices 221 may include, for example, a keyboard, touch screen, a remote control pad, a pointing device (such as a mouse, touchpad, stylus, trackball, or joystick), a scanner, a camera or a microphone. The output devices 223 may include, for example, a monitor display, television, printer, stereo, or speakers.

Still further, the computing unit 203 may be directly or indirectly connected to one or more network interfaces 215 for communicating with a network. This type of network interface 215, also sometimes referred to as a network adapter or network interface card (NIC), translates data and control signals from the computing unit 203 into network messages according to one or more communication protocols, such as the Transmission Control Protocol (TCP), the Internet Protocol (IP), and the User Datagram Protocol (UDP). Network adapters may be wireless or wired or combinations thereof. These protocols are well known in the art, and thus will not be discussed here in more detail. An interface 215 may employ any suitable connection agent for connecting to a network, including, for example, a wireless transceiver, a power line adapter, a modem, or an Ethernet connection. Connection agents may similarly be wireless or wired or a combination thereof. Accordingly, using interface 215, computer 201 may be able to access wide area networks such as the Internet in addition to local area networks. In one or more arrangements, a user may browse websites or other network devices through a local or wide area network using interface 215. Data such as physical activity may be transmitted to or received from local or remote network sources (e.g., devices 103a, 103b, 103c, 105a and 105b of FIG. 1).

Other peripheral devices may be included with or otherwise connected to a computer 201 of the type illustrated in FIG. 1, as is well known in the art. In some cases, a peripheral device may be permanently or semi-permanently connected to the computing unit 203. For example, with many computers, the computing unit 203, the hard disk drive 217, the removable optical disk drive 219 and a display are semi-permanently encased in a single housing. Still other peripheral devices may be removably connected to the computer 201, however. The computer 201 may include, for example, one or more communication ports through which a peripheral device can be connected to the computing unit 203 (either directly or indirectly through the bus 213). These communication ports may thus include a parallel bus port or a serial bus port, such as a serial bus port using the Universal Serial Bus (USB) standard or the IEEE 1394 High Speed Serial Bus standard (e.g., a Firewire port). Alternately or additionally, the computer 201 may include a wireless data "port," such as a Bluetooth interface, a Wi-Fi interface, an infrared data port, or the like.

It should be appreciated that a computing device employed according to various examples of the invention may include more components than the computer 201 illustrated in FIG. 2, fewer components than the computer 201, or a different combination of components than the computer 201. Some implementations, for example, may employ one or more computing devices that are intended to have a very specific functionality, such as a digital music player, an activity monitoring device or server computer. These computing devices may thus omit unnecessary peripherals, such as the network interface 215, removable optical disk drive 219, printers, scanners, external hard drives, etc. Some implementations may alternately or additionally employ computing devices that are intended to be capable of a wide variety of functions, such as a desktop or laptop personal computer. These computing devices may have any combination of peripheral devices or additional components as desired.

Figure 3:
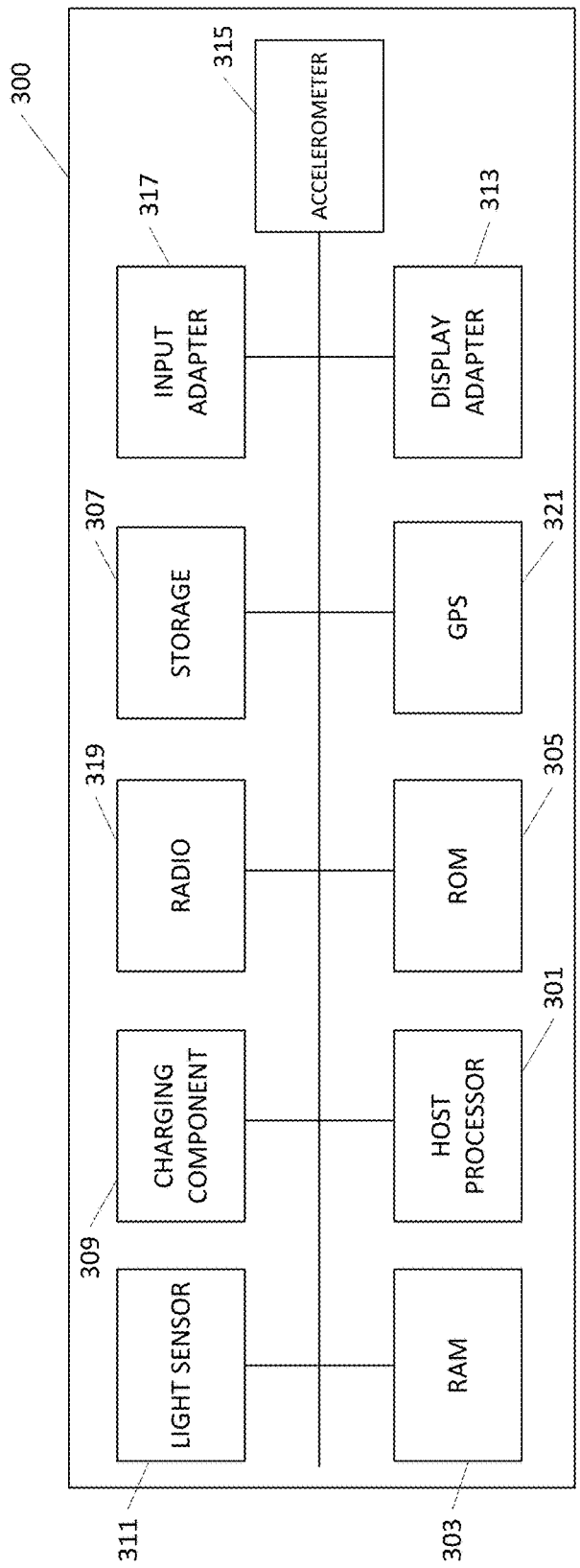
FIG. 3 illustrates another example device in which various features discussed herein may be included and/or implemented.

FIG. 3 illustrates another example computing device which may be applied to an activity monitoring device such as devices 103a, 103b and 103c of FIG. 1. For example, activity detection and tracking device 300 may include a variety of components including a main controller or host processor 301 configured to execute instructions and control other components of the device 300 in accordance with the instructions. The device 300 may further include memory for storage of data and instructions including volatile and non-volatile memory such as random access memory (RAM) 303, read-only memory (ROM) 305 and storage 307. Additionally, the device 300 may include a charging component 309 for charging one or more batteries (not shown) powering the device 300. The device 300 may further include various input and output adapters and other components including an ambient light sensor 311, a display adapter 313, an accelerometer 315 and input adapter 317. Ambient light sensor 311 may be used to determine a level of brightness for one or more displays for viewability. Light sensor 311 may also be used to determine a general time of day. Input adapter 317 may be configured to receive and process various types of input including button presses, touch input, scroll wheel input and the like, depending on the types of input devices included in the device 300. Accelerometer 315 may be configured for detecting movement of the wearable device and the user when the device is worn. In some examples, accelerometer 315 may be a one-axis, three-axis or six-axis accelerometer. Other sensors including heart-rate sensors, temperature sensors, humidity sensors, compass, gyroscopic sensor and the like may also be included in the device 300.

Communication by the device 300 may be performed through wired and wireless connection means. In one example, device 300 may include a radio component 319 configured to communicate with other devices wirelessly through radio frequency transmissions. The radio component 319 may correspond to a BLUETOOTH transceiver, an RFID device, a Wi-LAN transceiver, cellular transceiver and the like and/or combinations thereof, and/or may include a dedicated processor. Display adapter 313 may be configured to control one or more displays of the device in conveying various activity information, interaction information, alerts, notifications and the like. In one example, display adapter 313 may be configured to control a first display independently from controlling a second display of the device 300. The wearable device may further include location determination components such as global positioning system (GPS) component 321. Location determination may also be performed using other devices including a cellular transceiver (e.g., based on cellular triangulation). Components described herein may be combined into a single device or may be distributed over multiple components. Moreover, additional or alternative components may be used to provide additional or alternative functionalities.

A multi-activity platform and system such as system 107 may be configured to receive physical activity data for multiple different types of activities and multiple activity sessions from a variety of different monitoring/detection devices and types of monitoring/detection devices. The various functionalities provided by the system may include: activity data tracking and processing, facilitating activity challenges, interfacing with legacy activity tracking systems, generating community information including activity statistics for an entire community, device configuration, setup and synchronization, tracking and processing goals, user registration, interfacing with other communities or social networks to obtain or provide relevant information, user profile and site management and the like.

While the multi-activity platform and system 107 is described as being separate from devices 103a, 103b, 103c, 105a, 105b and 105c, all or a portion of the multi-activity platform may be implemented in devices 103a, 103b, 103c, 105a, 105b and 105c. For example, the multi-activity platform may include an application protocol interface configured to facilitate data communication and interactivity between different activity monitoring devices, tracking services or systems, activity monitoring applications and the like. As such, regardless of the configuration or type of the activity monitoring device (e.g., types of sensors included or type of activity to be tracked), tracking service or system or applications executed thereon, data may be communicated and functions may be invoked using a shared framework.

Figure 4:
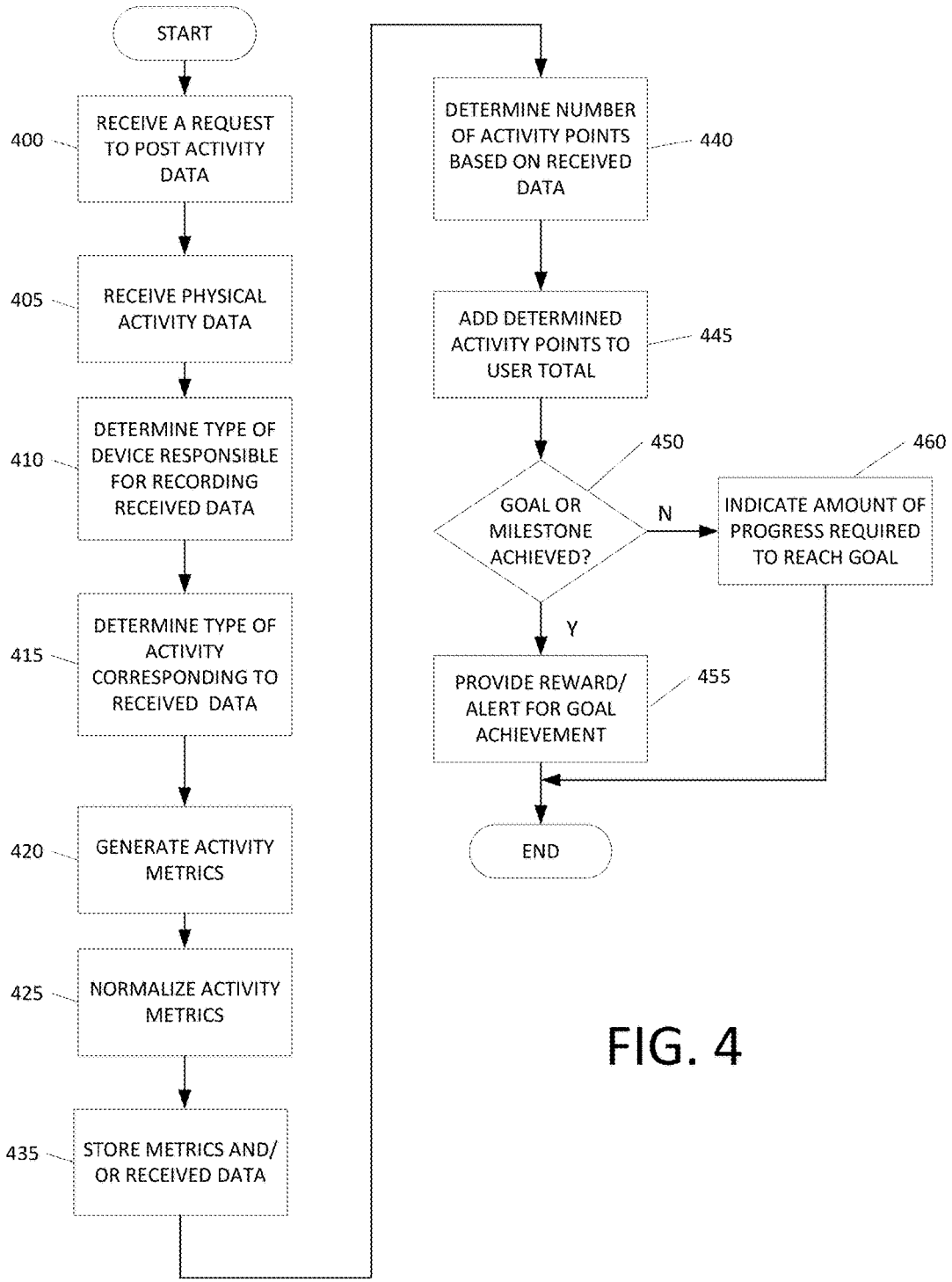
FIG. 4 is a flowchart illustrating an example method for processing multiple types of activity data from a variety of device types according to one or more aspects described herein.

FIG. 4 illustrates an example process through which a multi-activity platform and system may process activity data from multiple devices and for multiple activities. In step 400, the system may receive a request to post data to the system. The request may be received from an activity detection and monitoring device such as devices 103a, 103b and 103c (FIG. 1) or from an intermediary device such as computing devices 105a and 105b (FIG. 1). In step 405, the system may receive the physical activity data from the requesting device. The physical activity data may be transmitted according to various protocols and, in at least one example, may be transferred using an API provided by the system, as discussed in further detail herein. In step 410, the system may determine a device type of an activity detection and monitoring device responsible for recording the physical activity data. Device types may be indicative of device capabilities, a type of activity for which the device type is configured for use, device components, data accuracy, data recording parameters (e.g., how frequently data is collected), and the like and/or combinations thereof. The device type may be determined based on various parameters specified in the request (e.g., a device type parameter in a data posting function of the API) or based on an analysis of the physical activity data received. For example, the system may determine if the physical activity data received includes accelerometer data, heart rate data, GPS data and the like. Based on predefined rules, the system may then determine whether the types of data in the physical activity data correspond to a first device type or a second device type. In another example, the system may receive a device identifier such as a user specified name, a brand, a product name, a serial number and the like and determine the device type based thereon. In a particular example, the device identifier may be pre-associated or registered with the device type at a time of device registration. Various other manners of determining device type may also be used as needed or desired.

In step 415, the system may further determine a type of activity associated with the received physical activity data. In one example, this determination may be made based on the type of device from which the data was received. For instance, a first type of device may be configured for a first activity type such as basketball while another type of device may be configured for a second activity type such as running or walking. In another example, the activity type determination may be determined based on a data parameter received by the system. The parameter may be user-specified by a user tagging the activity data with the type of activity performed or may be tagged by one or more devices based on activity type recognition algorithms and methodologies. In one example, a device such as the activity detection and monitoring device may compare the pattern of physical activity data to previous sets of physical activity data and determine similarities. Upon determining that the pattern of physical activity is of a predefined threshold match with a previous set of physical activity data (of a known activity type), the device may determine that the recently recorded physical activity corresponds to the same activity type. Various other functions, algorithms and methods may be used for determining activity type.

In step 420, the system may be optionally configured to generate activity metrics for the physical activity data received. Metrics may include time, pace, distance, heart rate, body temperature, steps taken, calories burned and the like. In some arrangements, the physical activity data may already include metrics generated by the activity detection and monitoring device or an intermediary computing device. Accordingly, the system may be configured to determine whether metrics have already been generated or included in the received activity data and if not, generate the metrics. However, if the metrics are already generated/included, the system might not generate metrics. In other arrangements, the physical activity data may be raw sensor data that has not been processed into metrics. Accordingly, if the latter, the system may process the raw sensor data into one or more metrics. For example, for accelerometer data and running activities, foot contact time may be identified from sensor data according to various known methodologies, and pace, distance and speed may be calculated therefrom. The metrics may be generated using algorithms and methods selected based on the device type and/or the type of athletic activity performed. For example, different device types may have different calibration values while data for different types of athletic activity may correspond to different types of metrics. Different device types may also have different sensors and thus require different types of algorithms for processing the sensor data.

In step 425, the system may further normalize the activity metrics determined from the activity data. Normalization may be performed to compensate for discrepancies in data accuracy between different devices, different device types, different activity sessions, different activity types and the like. Normalization may be performed using predefined tables or normalization (e.g., calibration) values for adjusting metrics determined for certain types of activities or types of devices. Thus, distance run as determined using a first activity monitoring device may be multiplied by a factor of 1.05 while distance run as determined using a second activity monitoring device may be multiplied by a factor of 0.998. These normalization or calibration values may be determined based on empirical analysis in one or more arrangements. In other examples, normalization and calibration values may be determined based on statistical analyses by asking a user to perform a specified activity (e.g., run 200 feet) and recording and analyzing the resulting data.

In step 440, the system may determine a number of activity points to award the user based on the received physical activity data. In one example, a table may be used to define a number of activity points to award to a user based on various types of metrics, metric values, device types and activity types. For example, a different number of activity points may be defined for different device types, different activity types or different combinations of device types and activity types. The metrics and/or raw activity data may also be stored (see, e.g., step 435). In some arrangements, activity characteristics such as altitude, terrain, temperature, and weather (e.g., rain, snow, sun) may also be used in the activity point determination process. In one example, a higher activity point accumulation rate may be used for activities at higher altitudes and/or harsher weather conditions (e.g., accumulation rate higher for snow than rain than sun). These accumulation rates may, in some arrangements, be user-configurable for each of the activity characteristics and/or combinations of activity characteristics.

Once the number of activity points has been determined, the activity points may be added to a total number of activity points for a particular time period in step 445. For example, activity points may be accumulated to achieve a goal during a goal time period (e.g., 1 hour, 12 hours, a day, 2 days, a week, etc.) As such, in step 450, the system may determine whether the user has achieved a goal, reached a milestone or the like based on an amount of activity points accumulated. For example, a user may have a 3,000 activity point goal for the day. Accordingly, the system may determine whether the user has achieved 3,000 activity points for the day. In another example, a milestone may be defined as reaching 25,000 lifetime activity points. Accordingly, the system may determine whether a total of all lifetime accumulated activity points has reached 25,000. As such, different activity point counts may be kept for different time periods.

If the user has reached a goal or achieved a milestone, a reward or alert may be provided to the user in step 455. The reward may include virtual items, services, coupons, tickets, currency, virtual currency, items for an avatar and the like. If a goal has not been achieved or a milestone not reached, the system may indicate an amount of progress still required (e.g., a number of activity points needed) to reach the milestone or goal in step 460.

In addition to receiving data from devices, the system may also be configured to transmit data to devices. For example, synchronization of data between the system and one or more monitoring devices may include transmitting physical activity data recorded by a first monitoring device to a second monitoring device and/or downloading historical activity data recorded by the first monitoring device back to the first monitoring device. In some instances, not all data may be transmitted from one monitoring device to another and instead, data may be filtered based on data compatibility, activity type, user performing the activity and the like. For example, a receiving device may be required to have the capability to record the same type of data (e.g., have the same type of sensor) as the data to be synchronized from the transmitting device. In another example, data might only be synchronized if the receiving device is configured to track and/or monitor an activity type corresponding to the data. Various other rules may be used to process synchronization requests. Activity points may always be synchronized so long as the receiving device has the ability to track activity points.

In some examples, transmission and synchronization of data between two monitoring devices may be facilitated by the multi-activity platform and system. For example, the system may be configured to convert data sent using a first communication protocol with which a receiving device is incompatible to a second communication protocol with which the receiving device is compatible. Additionally or alternatively, the content of the data may be modified by the system according to formatting requirements of the receiving device (e.g., character limits, image sizes, number formats, date formats, etc.) and data storage structures or parameters of the receiving device. In one example, user profile information may be automatically imported from one device to another device. Various data fields available on the first device might not exist on the second device and thus, the system may filter out data for those fields prior to synchronizing the information to the second device. The system may be configured to perform a variety of other data and protocol manipulation functions to provide compatibility between two devices.

As discussed, an activity monitoring device such as device 103*a*, 103*b* or 103*c* may initially detect and store activity data and subsequently synchronize the data with one or more of a local device/application (e.g., device 105*c*) and/or a remote multi-activity system/server (e.g., system 107). In one arrangement, the multi-activity system/server may represent a destination or preferred storage site due to a larger storage capacity. Accordingly, data recorded by the activity monitoring device and/or synchronized to a local device/application such as device 105*c* may be ultimately transferred to the multi-activity system/server for long-term storage so as not to require and/or occupy large data storage capacities in the monitoring device and/or the local device. The local device may be a mobile communication device such as a smart phone, a portable media device, tablet computer, netbook computer, or laptop computer and/or a stationary device such as a desktop computer.

In some arrangements, an intermediary device such as device 105*a* may execute a synchronization application configured to synchronize data between the activity monitoring device and the multi-activity system/server. Such an intermediary computing device and synchronization application might not be configured to synchronize data between the intermediary device and the activity monitoring device. Instead, the synchronization application might only synchronize data between the activity monitoring device and the multi-activity system/server and only provide such synchronization functionality when a connection to the multi-activity system/server is available. In another example or arrangement, a local application/device may synchronize activity data from the activity monitoring device independently of synchronizing the data with the multi-activity system/server. Once a network connection is available with the multi-activity system/server or when the user elects to synchronize with the multi-activity system/server, the data may be subsequently synchronized to the multi-activity system/server from the local device/application.

Other synchronization processes may also be used. For example, a local device/application may synchronize data through the intermediary application/device. In yet other examples, the activity monitoring device may be configured to communicate directly with the multi-activity system/server (e.g., without first communicating with the local device/application or the intermediary application/device) and synchronize data therewith. As well, the one or more intermediary devices, with or without any local device(s), may synchronize among any combination thereof, e.g., depending on connectivity, the desirability to keep such combination(s) of devices in synchrony or otherwise. The activity monitoring device may or may not be synchronized together with any such combinations of intermediary and/or local device(s). The multi-activity system/server may or may not be synchronized together with any such combinations of intermediary and/or local device(s) and/or activity monitoring device.

In order to reduce the amount of overlap in data transmitted and synchronized, various parameters/settings may be defined to track the data that has been synchronized to the multi-activity system/server and to a local device/application. In one example, the activity monitoring device may store two parameters: a local read offset (LRO) and a local read time stamp (LRTS). The local read offset (e.g., memory location identifier) may indicate the offset in the activity monitoring device storage (e.g., flash memory) at which the local application/device should begin reading activity data from the monitoring device when synchronizing. For example, this memory location or offset may specify a location where a first unread activity data record is stored. In some arrangements, the LRO may represent a synchronization offset for the local application/device to which data is synchronized (versus the multi-activity system/server to which data might also be synchronized). The local read time stamp indicates the time stamp of the last sample read by the local application from the activity monitoring device storage. The time stamp may correspond to a time at which the sample (e.g., activity data) was recorded by the monitoring device. These parameters are set when (e.g., during or after) the local device/application synchronizes with the activity monitoring device. For example, the activity monitoring device may set and/or store the local read offset based on the memory location of the activity monitoring device storage last read by the local device. In particular, the local read offset may correspond to the offset of the last memory location read by the local device incremented by one position or memory location (e.g., the first new activity data memory location). As such, the LRO and LRTS may help the activity monitoring device, local application/device and/or the MSP track the data that has been read and/or the data that has not been read, so that read data is not re-transmitted needlessly to the local application/device during synchronization.

Additionally, the multi-activity service/system may define a last synchronization offset (LSO) and a last synchronization time stamp (LSTS). The LSO may refer to the offset (e.g., a memory location identifier) in the activity monitoring device's storage memory at which reading and synchronization of data to the multi-activity service/system should begin. The LSO may be different than the LRO if the local synchronization device has read more or less data than the amount of data that has been synchronized to the multi-activity service/system. In some examples, the LRO/LRTS may be updated independently of the LSO/LSTS and vice versa. That is, one set of parameters may be updated without updating the other. On the other hand, if the same data that has been synchronized to the multi-activity service/system has also been read by the local device/application, the LSO and the LRO may be the same.

The local device may update (or cause the activity monitoring device to update) the LRO and LRTS upon synchronizing data with the monitoring device. Moreover, the local device may update the LSO and LSTS, or cause the LSO and LSTS to be updated upon synchronizing data stored in the local device to the multi-activity service/system. In some examples, when the intermediary device/application conducts synchronization between the monitoring device/application and the multi-activity system/service, only the LSO and LSTS may be updated since the intermediary device does not, itself, store and synchronize any data. In such an event, the LRO/LRTS may also be updated to indicate to the local device that further data has been already been synchronized to the multi-activity service/system and that the local device does not need to further synchronize that data to itself. In one example, the intermediary device/application may initially request the LSO and LSTS from the multi-activity service/system and use the LSO and LSTS to determine a start point in the activity monitoring device's memory for reading data and synchronizing the data with the multi-activity service/system. In some arrangements, the LRO/LRTS might only be updated if the LSO/LSTS has been updated to a point beyond the LRO/LRTS (e.g., in a data storage progression). Using the above process, the multi-activity service/system may avoid receiving data (e.g., from the local device) that has already been synchronized to the multi-activity service/system in the past (e.g., directly from the monitoring device or through the intermediary device).

Additionally or alternatively, data of the monitoring device already synchronized to the multi-activity system/service may be deleted from the monitoring device. In another example, the data may be deleted if the multi-activity system/service has not been synchronized with that data; in such case of deleted data, a notification or indicator may be provided to the activity monitoring device, a local device, an intermediary device and/or the multi-activity system/server indicating that synchronization is to be performed with the local device storing the data that has yet to be synchronized with the multi-activity system/service However, data only synchronized to a local device, and not the multi-activity system/service, might not be deleted. Examples of circumstances in which data might not be deleted include, e.g., to maintain redundancy as to the synched data (such as until a selected time has elapsed or a selected event occurred, such as synchronization to a predetermined device or number of devices, or to the multi-activity system/service), or in the event the user wishes to later synchronize the data through the intermediary device/application instead of using the local device, and/or in the case the user wishes to synchronize additional local devices from the monitoring device. In other examples, the data may be deleted if the multi-activity system/service has not been synchronized with that data. Instead, a notification or indicator may be provided to the activity monitoring device, a local device, an intermediary device and/or the multi-activity system/server indicating that synchronization is to be performed with the local device storing the data that has yet to be synchronized with the multi-activity system/service. Data synchronized to the multi-activity system/service might not be deleted from the activity monitoring device in some instances if, for example, the data has not yet been synchronized to the currently proximate local device/application. The deletion of data from the activity monitoring device may be configurable by the user. Alternatively or additionally, data may be deleted once synchronized to the multi-activity system/service and/or to any other device in the event that the amount of space remaining on the activity monitoring device decreases below a specified threshold.

According to other aspects, data from an activity monitoring device may be synchronized to multiple local devices. In such a configuration, each local device may set to a different set of LRO and LRTS markers unique to that local device.

In yet other arrangements, if a local device determines that the user is attempting to synchronize a threshold amount of data from the monitoring device, the local device may provide a message/recommendation to the user to use the intermediary device/application instead. This recommendation may be provided in circumstances where the intermediary device/application is configured to read data off of the monitoring device at a faster rate than the local device (e.g., USB vs. BLUETOOTH).

In yet other examples or arrangements, the above described offsets and synchronization processes may be activity type or device type specific. For example, a running LRO, LRTS, LSO and LSTS may be defined specifically for a buffer or storage area configured to store running data while a basketball LRO, LRTS, LSO and LSTS may be defined for a different buffer or storage area configured to stored basketball data. Similar offsets and/or storage areas may be defined for different data recording device types. Accordingly, applications that are configured to synchronize one type of activity or data from one type of device but not another may modify the offsets/parameters for only one of the storage areas/activity types/device types while not affecting the others. Such a configuration may add flexibility to synchronization capabilities.

By using the above noted offsets and timestamps, the amount of data that may be synchronized is optimized such that new or unsynchronized data is to be synchronized to a recipient device.

Monitoring Device Setup/Configuration

A multi-activity platform and system may further allow devices, systems and applications to setup and configure various types of monitoring devices. In some arrangements, an intermediary computing device such as device 105a or 105b may serve as a multi-activity system that is configured to communicate with and interact with a various monitoring devices and device types that may be configured to detect and monitor a variety of types of activity. For example, intermediary application or computing device may be used to register users or devices with a multi-activity service or system such as an on-line community or service. In a particular example, the intermediary application or computing device may be configured to register multiple different devices and device types.

Figure 5A:
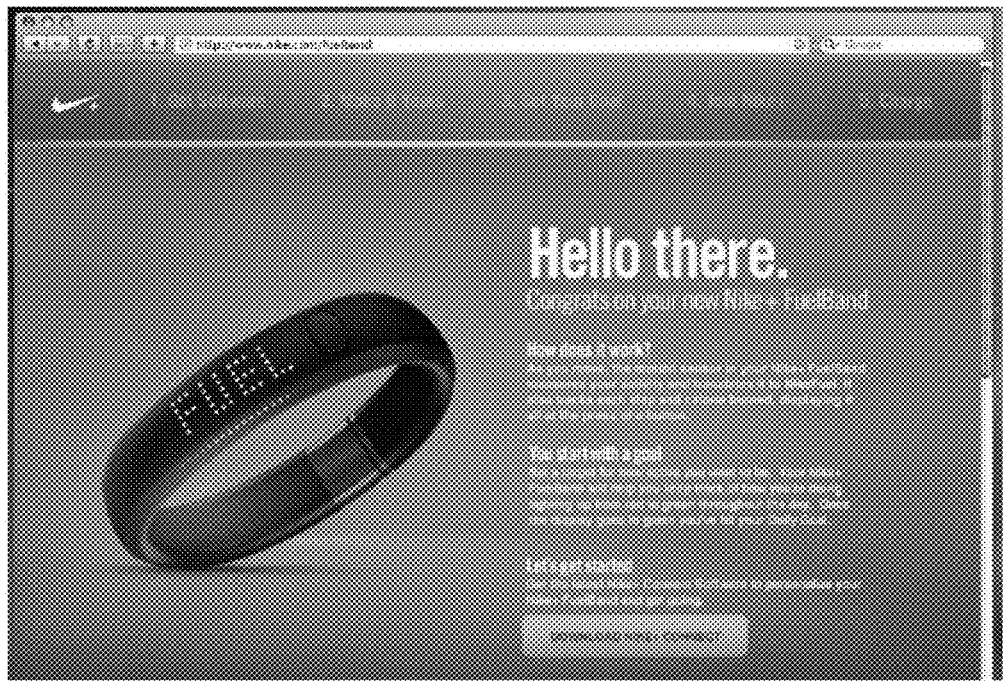
FIGS. 5A-5I illustrate example interfaces a device setup and configuration according to one or more aspects described herein.

FIGS. 5A-5E illustrate example interfaces for a device setup and configuration application that may execute on a user's local computing device to which an activity monitoring device may be connected. In one example, the application may be stored in the activity monitoring device and downloaded and installed to a user's device upon connection. Alternatively or additionally, the activity monitoring device may store a location identifier such as a URI with an instruction for the computing device to retrieve and install the data located at the URI. In still another example, as illustrated in FIG. 5A, the activity monitoring device may specify a URI where the device may be introduced and an option may be provided to download a corresponding application for configuring the device. The local computing device may then automatically navigate to the URI upon connection of the activity monitoring device.

Figure 5B:
Figure 5C:
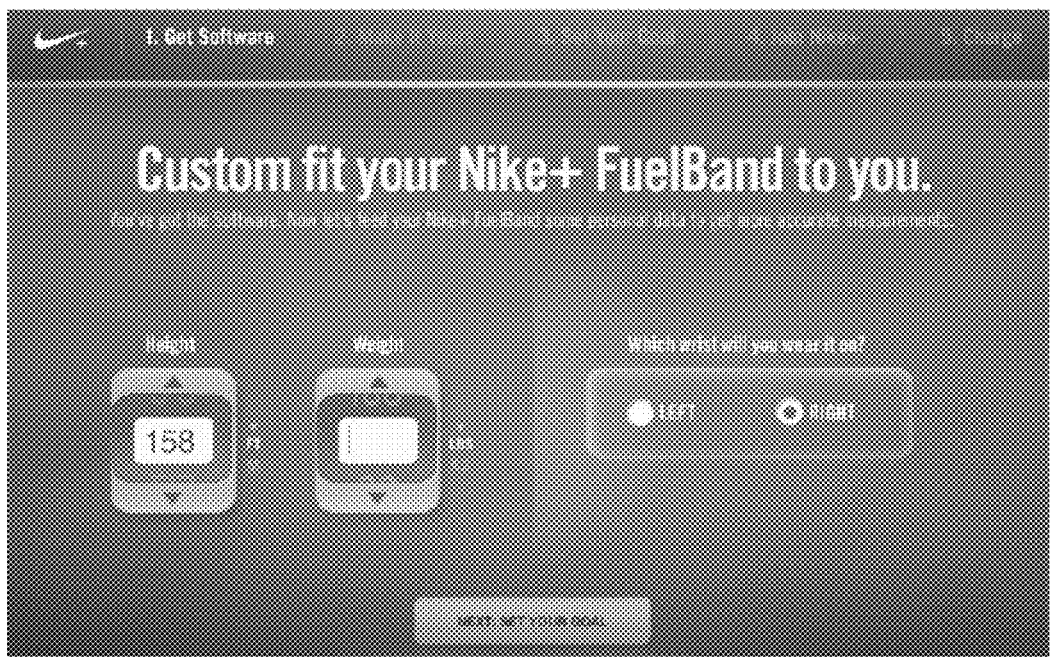
Figure 5D:
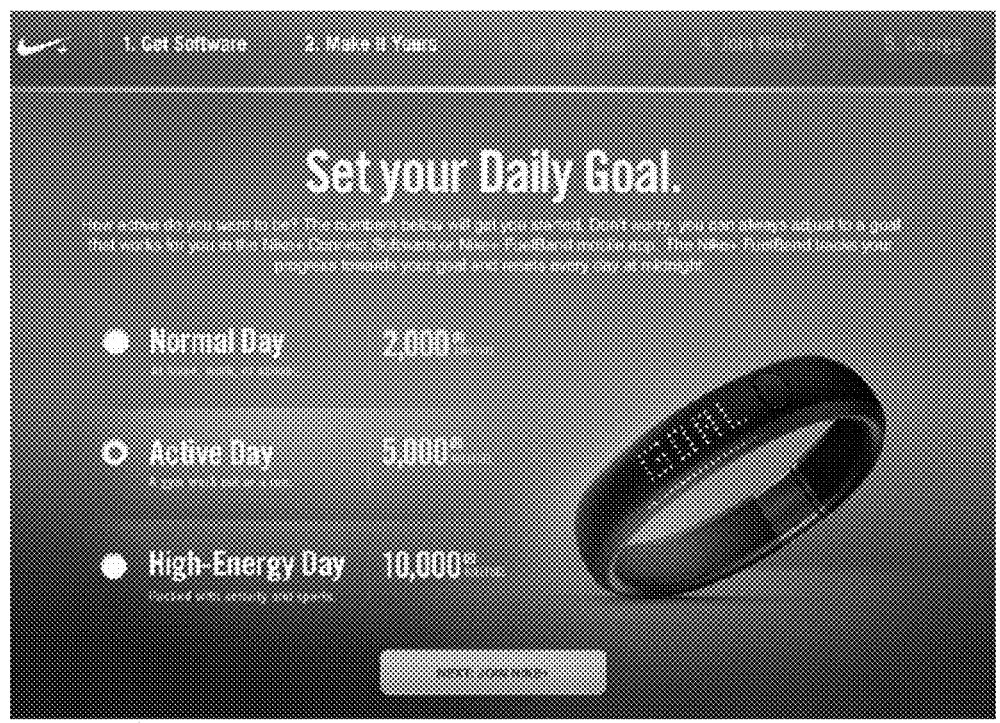

FIGS. 5B-5D illustrate example device configuration interfaces that may be provided upon downloading the device configuration application. FIG. 5C, for example, allows the user to specify user characteristics such as height and weight to help better calibrate the device as well as identify a wrist on which the device will be worn. Other types of user characteristics may be defined and provided as configuration options as desired or needed. For example, the device may be worn on other parts of the user's body. Age may also be added as a user characteristic for calibration purposes. In FIG. 5D, the user may be presented with an interface for setting an activity goal. The user may select any of multiple predefined levels or define his or her own goal manually (not shown). The goal may then be stored to the monitoring device for goal tracking and progress monitoring.

Figure 5E:

FIG. 5E illustrates an example interface through which a user may create or login to an on-line activity tracking and monitoring service. The user may be provided the option of registering a username specific to the service or using a login for an external site (e.g., an external social community network) as a login for the activity tracking and monitoring service. The various configuration and login information may be communicated to the monitoring device through the shared API as discussed herein. Additionally, a status of the device may be retrieved using the shared API as well. Other monitoring devices and device types may similarly be configured using the shared API. For example, the configuration and setup application may be configured to interact with multiple types of monitoring devices.

Figure 5F:
Figure 5G:
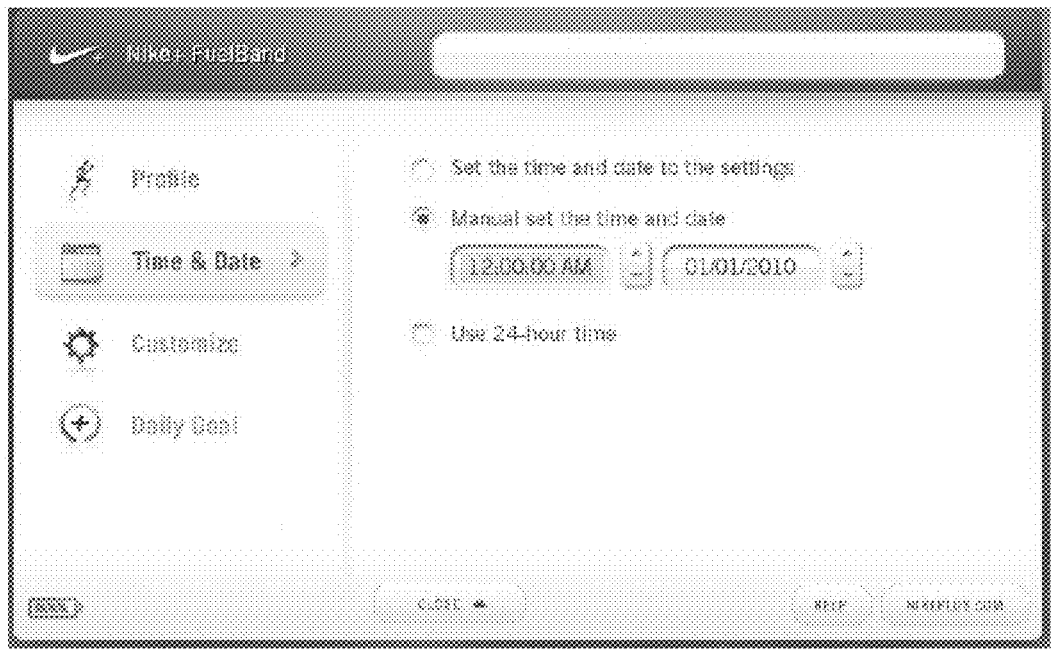
Figure 5H:
Figure 5I:

FIGS. 5F-5I illustrate further example application interfaces through which a user may configure an activity monitoring device. In FIG. 5F, for example, a user may specify his or her birthdate, gender, height and weight. In FIG. 5G, the user may further indicate how the device should obtain a time of day. The user may manually enter the time of day or may obtain time and date information from one or more other systems such as the computing device through which the device is being configured, a cellular system, a satellite and the like. The user may also indicate whether 24-hour or 12-hour time should be used. FIG. 5H illustrates an interface through which a user may select metrics that are to be displayed on the device. For example, a user may select to display calories, but not steps. Other settings may similarly be defined. FIG. 5I illustrates an interface through which a user may configure display options such as whether to use a goal indicator light and/or to include goal celebrations.

Various other configuration options may be added or removed as desired or needed.

The configuration application may be configured to interact and configure multiple different types of devices. Accordingly, the configuration interfaces may differ in content and/or appearance depending on the type of device connected. In one example, the application may identify the type of device connected and automatically execute the appropriate APIs and display the corresponding interfaces for the identified type of device. The different interfaces may offer different configuration options such as different displayable metrics, color configurations (e.g., if the device support color displays), display configurations (e.g., different options depending on a number of displays included in the device) and the like and/or combinations thereof.

Figure 6A:
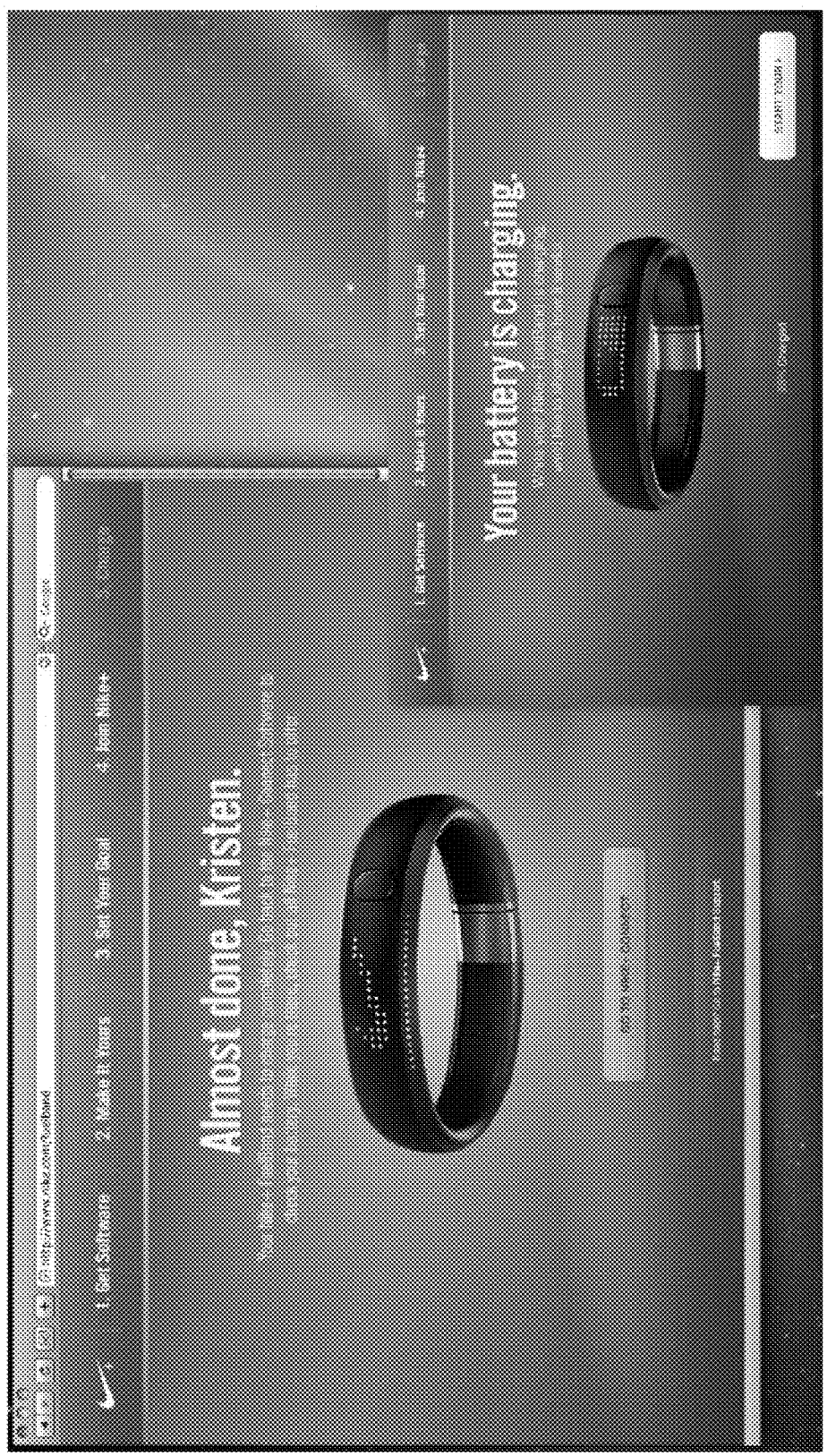
FIGS. 6A and 6B illustrate example interfaces conveying a battery charging status according to one or more aspects described herein.

FIG. 6A illustrates an example interface conveying a battery charging status of the device. In some examples, the device might not be useable for a first time until the device has reached a specific level of charge (e.g., 50%, 65%, 70%, 80%, 90%, 95%, 100%, etc.).

Figure 6B:
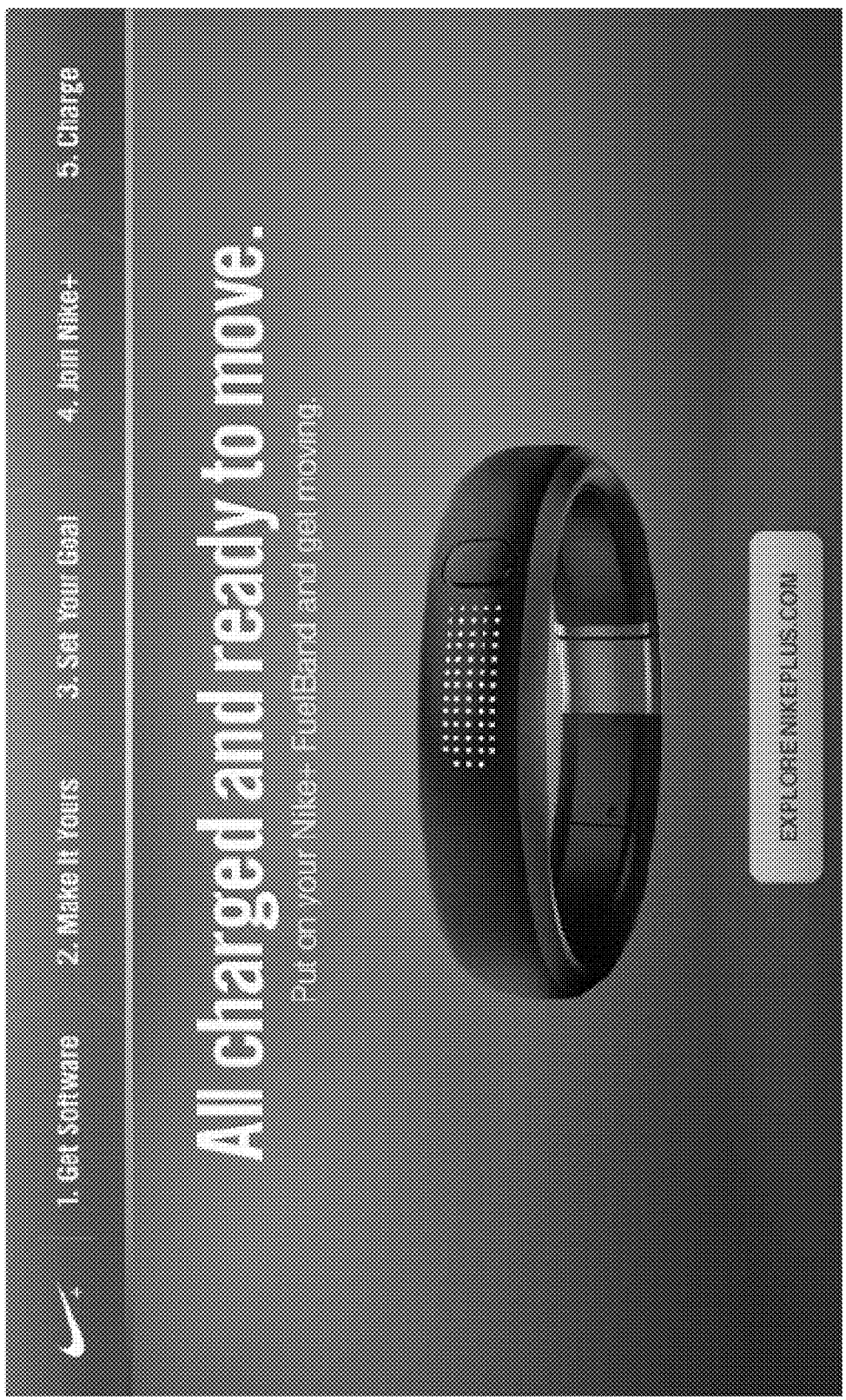

When the device has reached the requisite level of charge, a display such as the interface of FIG. 6B may be provided.

Figure 7:
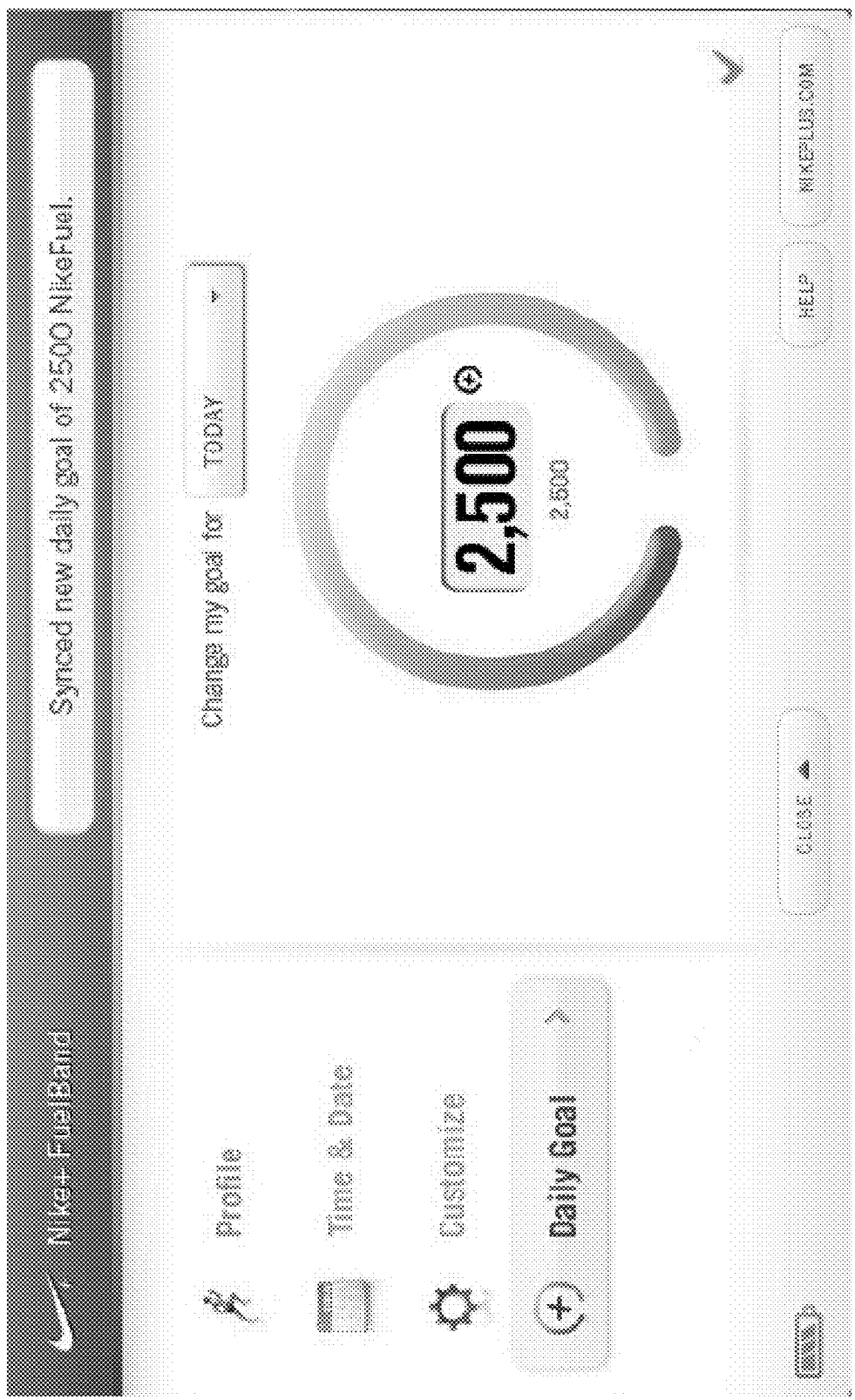
FIG. 7 illustrates an example configuration interface through which a user may define or redefine his or her goal according to one or more aspects described herein.

FIG. 7 illustrates another example configuration interface through which a user may define or redefine his or her goal. The user may change a goal for the current time period or for any other time period as desired. Once the user has confirmed a goal, the goal information may be synchronized to the user's device using the various shared APIs described herein.

Multi-Activity Community

A multi-activity system or service may include an on-line community or site that allows a user to review activity information for not only his or her activities but for other activities. The review may include a variety of information types including audio, video, text and the like. For example, motivational messages (e.g., user generated or system generated) may be provided to users through audio messages. Users may also record audio notes to be stored in association with one or more activity sessions, goal time periods or the like.

The on-line community or site may provide a user with different initial interfaces depending on the user's status. For example, if the user is new to the community, a first interface may be displayed. On the other hand, if the user is a returning user, a second interface may be present to the user upon login.

Figure 8A:
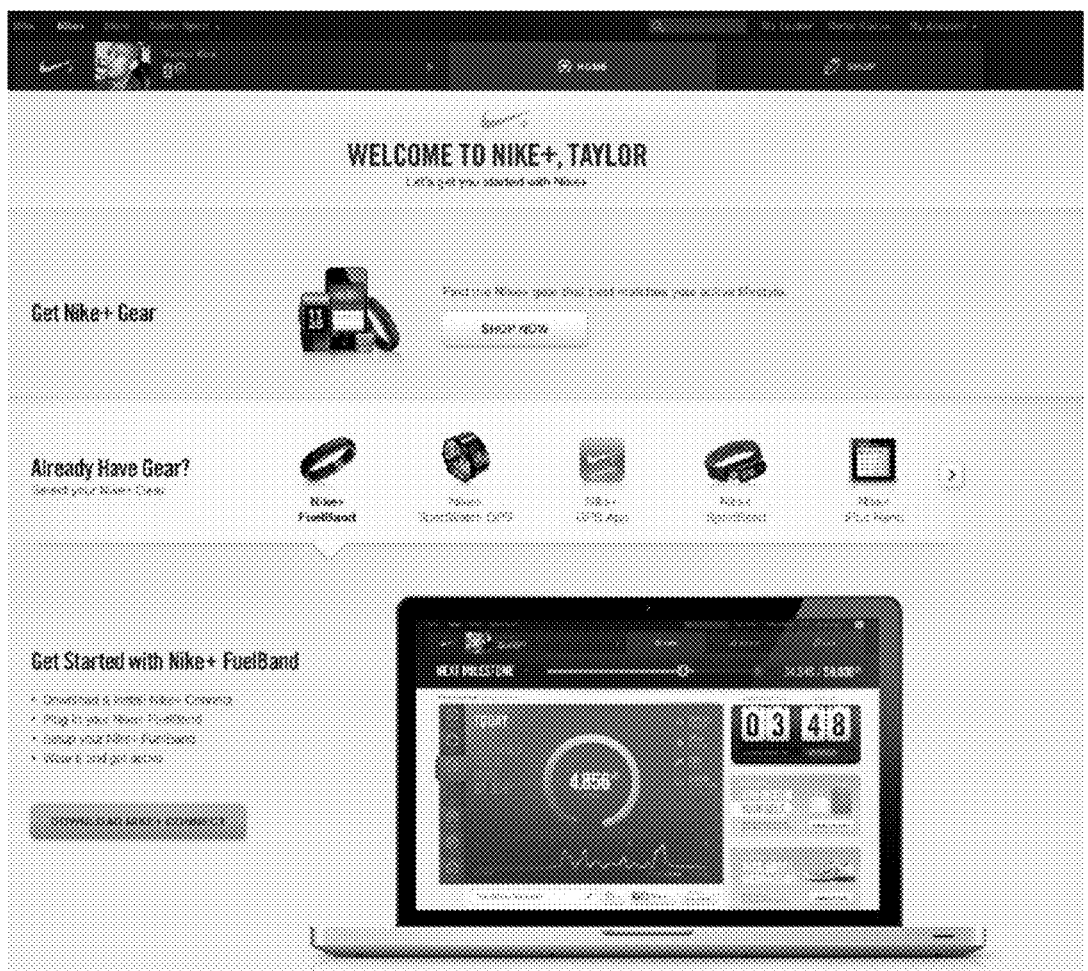
FIGS. 8A and 8B illustrate example welcome interfaces according to one or more aspects described herein.

FIG. 8A illustrates an example welcome interface that may be displayed for a new user on an on-line community or site upon user login. The interface may provide options to the user to purchase activity monitoring devices, or to specify the type of monitoring device or other equipment that the user already has purchased and/or will be using if known. In some arrangements, the registration/configuration application may automatically notify the on-line community of registered devices and thus, the welcome interface for users (regardless of new or returning) may acknowledge the existence of a registered device upon login. For example, the list of product recommendations might not include ones already purchased and/or registered. The interface of FIG. 8A may further provide a link to download a registration/configuration application. Again, if the user has already downloaded the application, the interface might not provide the link.

Figure 8B:
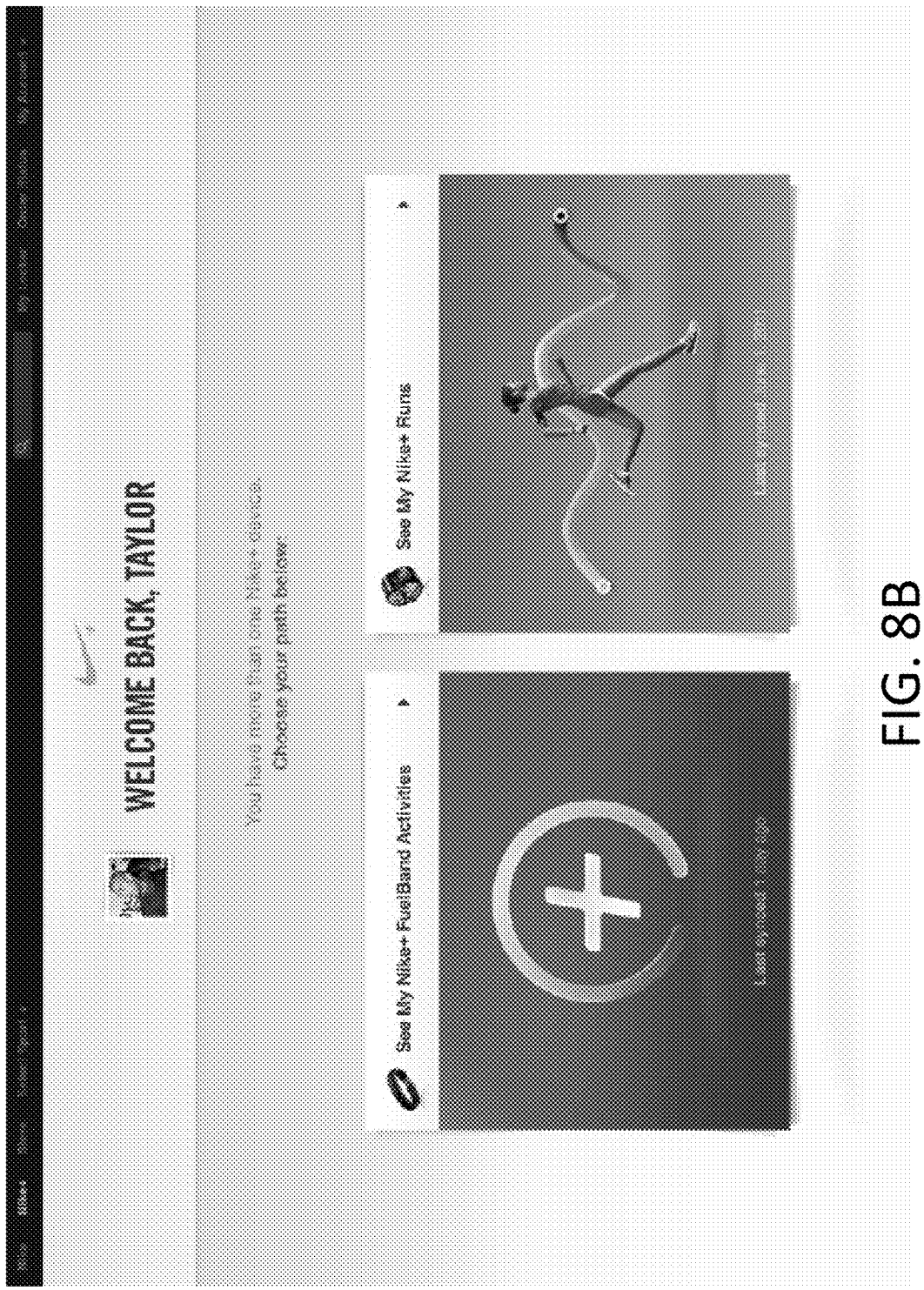

FIG. 8B illustrates an example welcome interface that may be displayed to an existing user of the on-line community/site. Instead of recommending products or providing options for downloading device applications, the interface may include options for viewing activity data. Activity data may be categorized based on type of activity and/or type of device used to record the activity data. Accordingly, the interface may provide multiple options for review of activity data depending on the types of activity in which the user has engaged and/or the types of devices the user has used to record his or her activity. As discussed herein, a multi-activity platform and system may be used to receive and differentiate between data of different activity types and device types. Accordingly, the on-line site/community may automatically recognize when different activity types and device types are represented in the activity data.

Figure 9A:
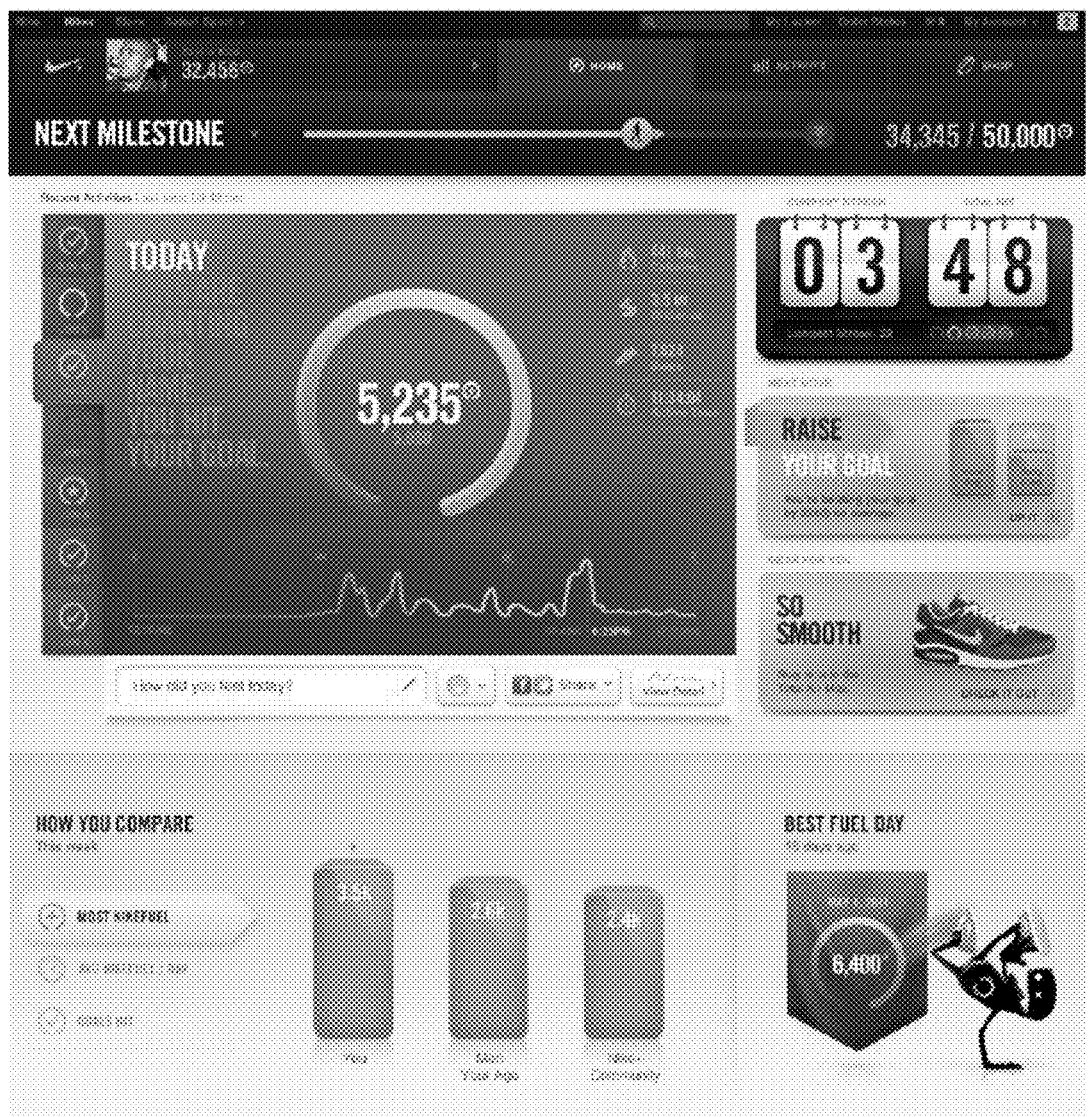
FIGS. 9A and 9B illustrate example interfaces that may be generated and displayed depending on the type of activity data that is to be viewed according to one or more aspects described herein.
Figure 9B:
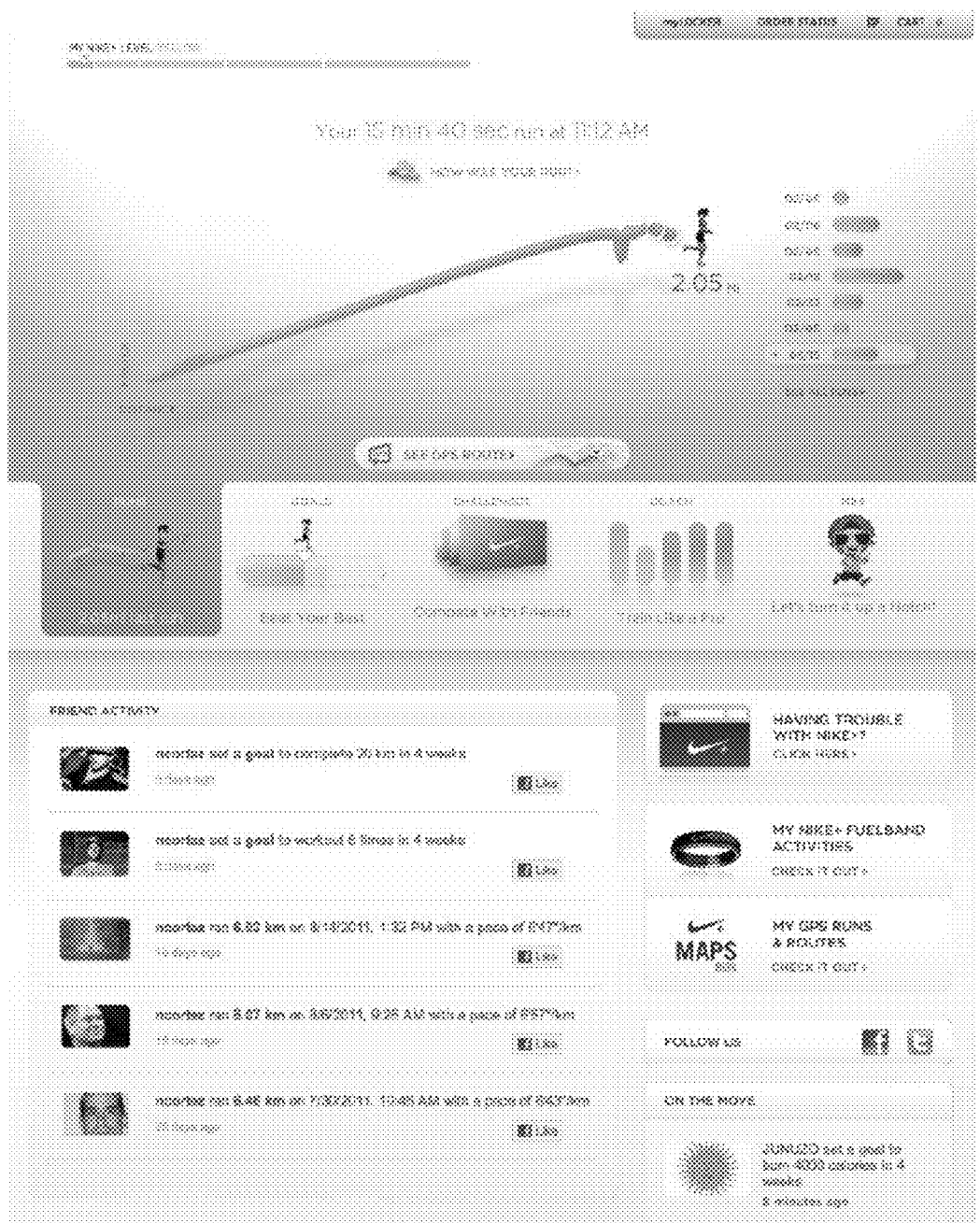

Additionally or alternatively, activity of different activity types or recorded using different device types may be visualized in different ways (e.g., colors, themes, interfaces, types of graphs, types of statistics, etc.). FIGS. 9A and 9B illustrate different interfaces that may be generated and displayed depending on the type of activity data that is to be viewed. FIG. 9A, for example, displays activity data recorded using a first type of monitoring device in a first type of visualization interface. Details of the interface are described in further detail herein. FIG. 9B illustrates a second type of visualization interface for visualizing activity data recorded using a second type of monitoring device. Types of devices may differ based on capabilities, calibration, types of sensors used, area on which the device is configured to be worn and the like. Accordingly, different visualizations and/or interfaces may be provided for different types of devices regardless of the type of activity performed (e.g., the types of activity recorded using the different types of devices may be the same or different). In a particular example, a first visualization or set of visualizations may be automatically generated upon uploading/receipt for data from a first type of device and/or a first type of activity performed while a second visualization or set of visualizations (different from the first visualization or first set of visualizations) may be automatically generated for data from a second type of device and/or a second type of activity performed. While the user may request additional types of visualizations (e.g., those provided as part of the first set of visualizations) for the second type device or second type of activity, only the second visualization or set of visualizations may be automatically provided as an initial set available upon upload/receipt of the data.

In other examples, various activity metrics may be viewed in a same interface or display regardless of the device type or activity type. For example, users may be able to track progress toward a goal that may be achieved through performance of multiple types of activities and regardless of the type of device that is used to record those activities. Additionally or alternatively, different graphs (e.g., line graphs, bar graphs, etc.) may be overlaid on the same chart/axes.

Figure 10A:
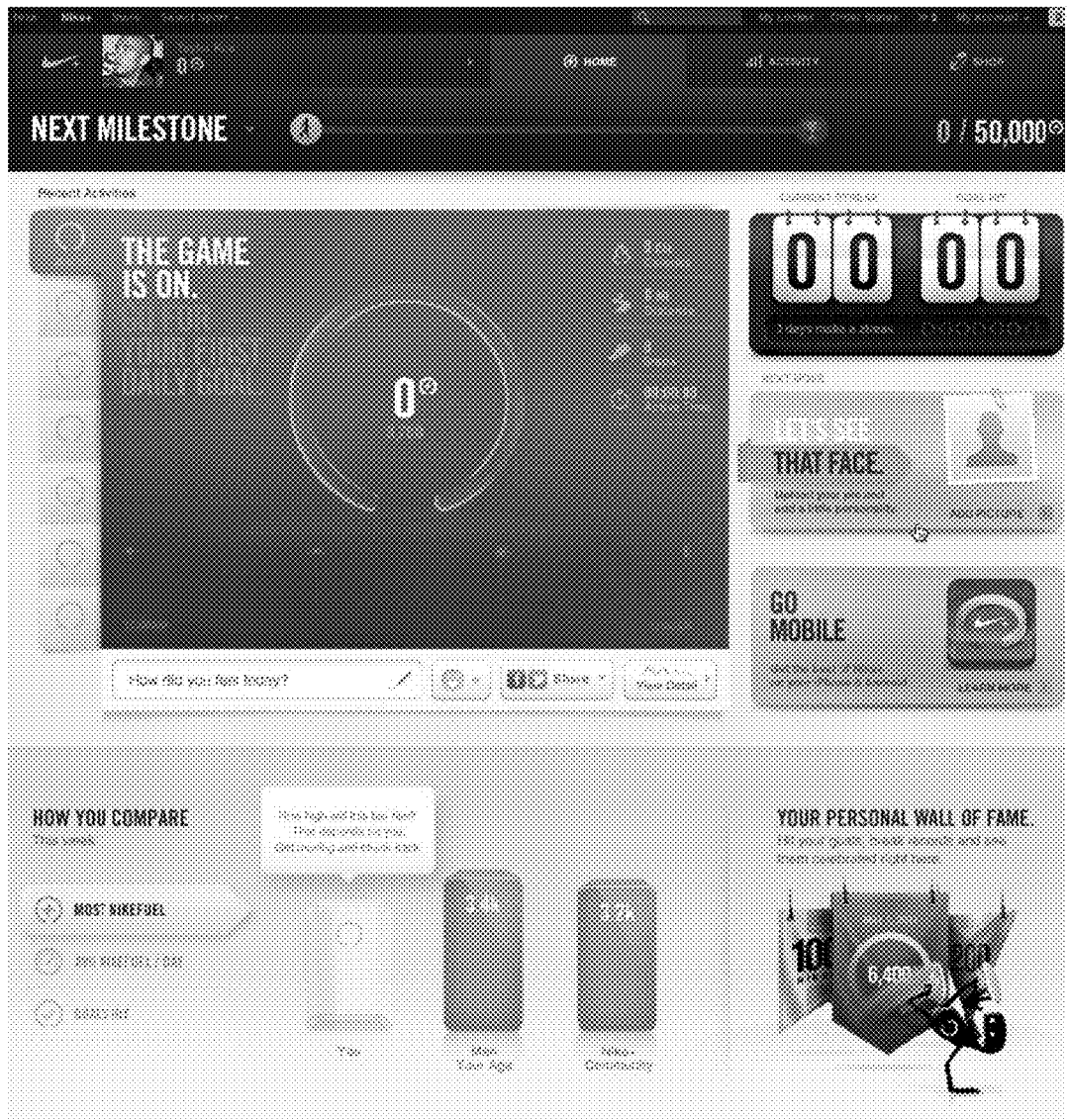
FIGS. 10A-10G illustrate example activity tracking and monitoring interfaces that may be used to track multiple types of activities and activities recorded using multiple types of monitoring devices according to one or more aspects described herein.

FIGS. 10A-10G illustrate example activity tracking and monitoring interfaces that may be used to track multiple types of activities and activities recorded using multiple types of monitoring devices. The interfaces may also be used to tag additional information about the various activities and activity sessions performed and to track progress toward an activity goal. FIG. 10A, for instance, illustrates an interface indicating that that user has recorded no activity and made no progress toward an activity goal. The interface of FIG. 10A may be displayed, for example, when a user first registers with the service and has not performed or synchronized any activity data with the on-line community. The interface may further display information such as an amount of progress toward a milestone. A milestone may differ from a goal defined for a specified goal period. For example, a goal period may be of a finite amount of time and goal progress may be determined based on activity performed during that finite amount of time. Goal time periods may also be recurring on a regular schedule. Milestones, on the other hand, may refer to achievements reached over a course of a user's lifetime of activity performed (e.g., reaching 50,000 activity points in the user's lifetime). Milestones may be unique. For example, each milestone might only be achieved once. Alternatively, milestones may be defined for finite time frames including a goal time period. In some examples, milestones may be defined for any time period different from a specified goal time period. In still other examples, milestones and achievements may relate to metrics other than a goal metric. Additionally or alternatively, milestones may also be uniquely generated/defined for each user based on user characteristics, interests, etc. For example, if a user enjoys running versus playing basketball, a distance milestone may higher than for a user when enjoys playing basketball more than running. Milestones may further differ for varying ages or age groups. Various configurations of milestones and goals may be used.

The activity tracking interface may further include a section comparing a user's performance against users of the community and/or groups of users in the community. For example, in FIG. 10A, the user's weekly activity points are compared against the entire community of users as well as a community sub-group of men of the same age as the user. The user may configure (e.g., select and/or define) the sub-groups and number of sub-groups to which his or her performance is to be compared. The user may further configure the activity time period to be compared (e.g., daily, weekly, monthly, etc.).

Figure 10B:
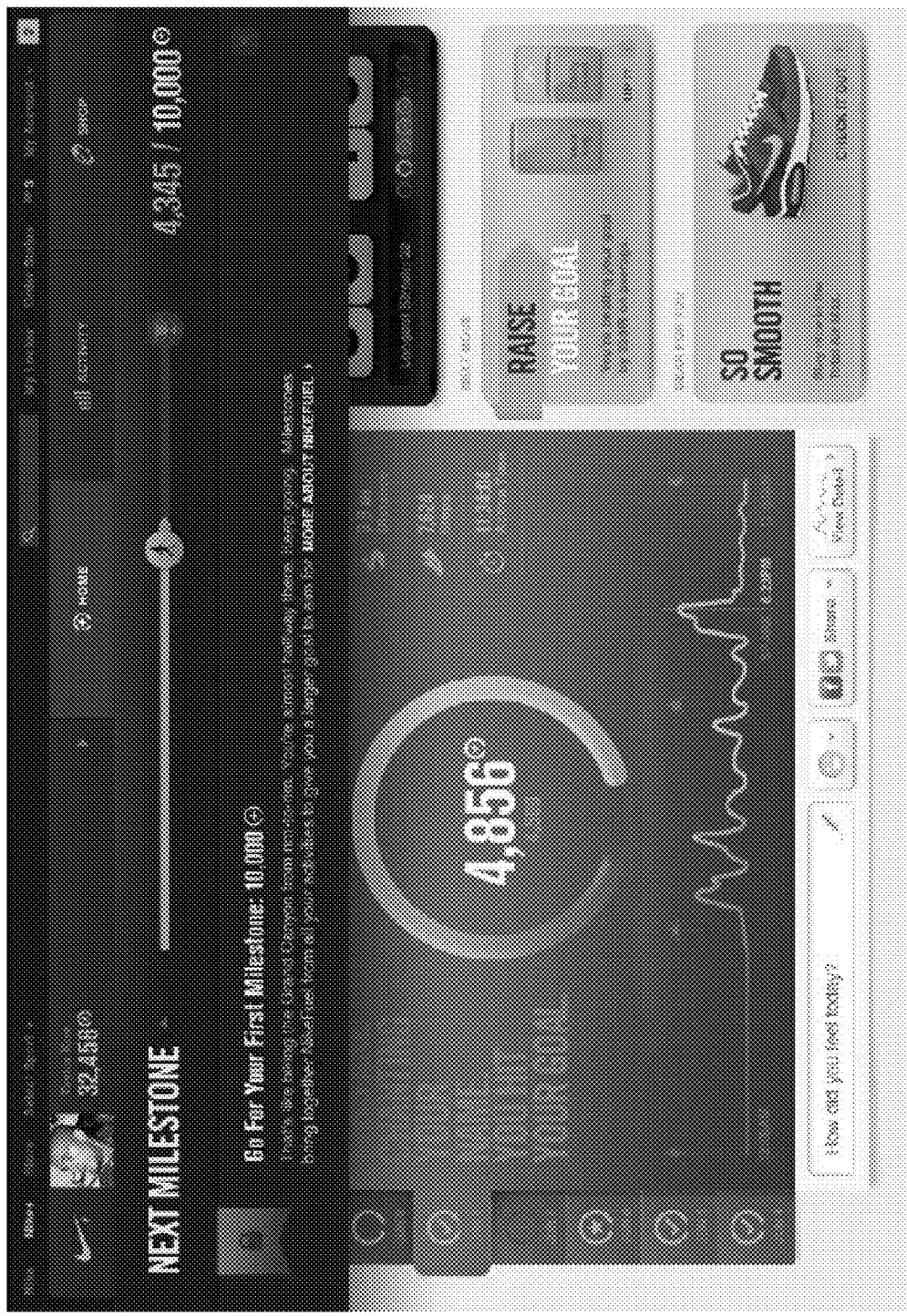

FIG. 10B illustrates an interface that may be displayed when a user has recorded and synchronized activity data. As shown, the interface indicates that the user has made progress toward a milestone of accumulating 10,000 activity points over the user's lifetime. The interface may also include an option to view subsequent milestones. Milestones may be consecutive or progressive in nature such that a user must complete a first milestone before reaching a second milestone.

Figure 10C:

FIG. 10C illustrates another interface displaying a user's progress made toward a goal as well as a milestone. Other activity summary information may also be provided including whether a streak has been achieved and a length of the streak, a number of goals reached, and various metrics for a selected goal time period. In one example, a section of the interface may display detailed metrics and activity information for a selected goal time period. Different goal time periods may be displayed as selectable section labels along a side of the display section. In addition to identifying the goal time periods (e.g., days, hours, weeks, etc.), the section labels may also display a progress made toward the goal for those time periods. For example, the section labels may indicate whether the user completed the goal by that day, whether a moderate amount of progress was made toward the goal (but not completed) or if a low level of progress was made toward the goal. Other indicators may also be included as part of the goal time period section labels. For example, if a user reached a milestone during that goal time period, another symbol or indicator may be displayed. In another example, if a user exceeded his or her goal by a specified amount, yet another symbol or indicator may be used as indication. Different colors, indicators, patterns, symbols, characters, transparencies and the like may be used to differentiate between goal progresses, other achievements, events and the like.

The activity detail display for a goal period may include a goal meter that indicates whether the user met his or her goal and if not, an amount of progress made towards the goal. In addition, a graph may be displayed to illustrate a breakdown of activity level over the goal time period. Various peaks in activity may also be identified in the graph with an indicator such as "SPARK." Peaks may be defined by an activity level exceeding a threshold amount of activity, the top number of activity levels in the goal time period, and the like. For example, the top 1, 2, 3, 4, 5, 10 peaks may be indicated in the graph. Various metrics may also be displayed in a portion of the detail display such as calories burned, distance traversed, steps taken and/or time active. Another portion of the display may display a current streak (e.g., a current number of consecutive goal time periods in which the goal has been reached) and a number of goals hit in the user's lifetime (or a specified time period). This portion of the display may display a streak tracker that provides an indication of a number of consecutive goal time periods including a current goal time period and a goal progression status for each of those time periods. The interface may also identify the longest streak the user has achieved. Alternatively or additionally, the system may also provide an indication of a number of streaks achieved. In yet another portion of the interface, the display may provide a recommendation for raising or lowering the goal. For example, if a user has exceeded previous goals by a specified amount (e.g., an average amount by which the user exceeded one or more previous goals, an accumulated amount by which the user exceeded the one or more previous goals, a greater, median or lowest amount by which the user exceeded one or more previous goals, etc.), the system may recommend that the user increase a next goal (e.g., by that specified amount or an even greater amount).

Figure 10D:
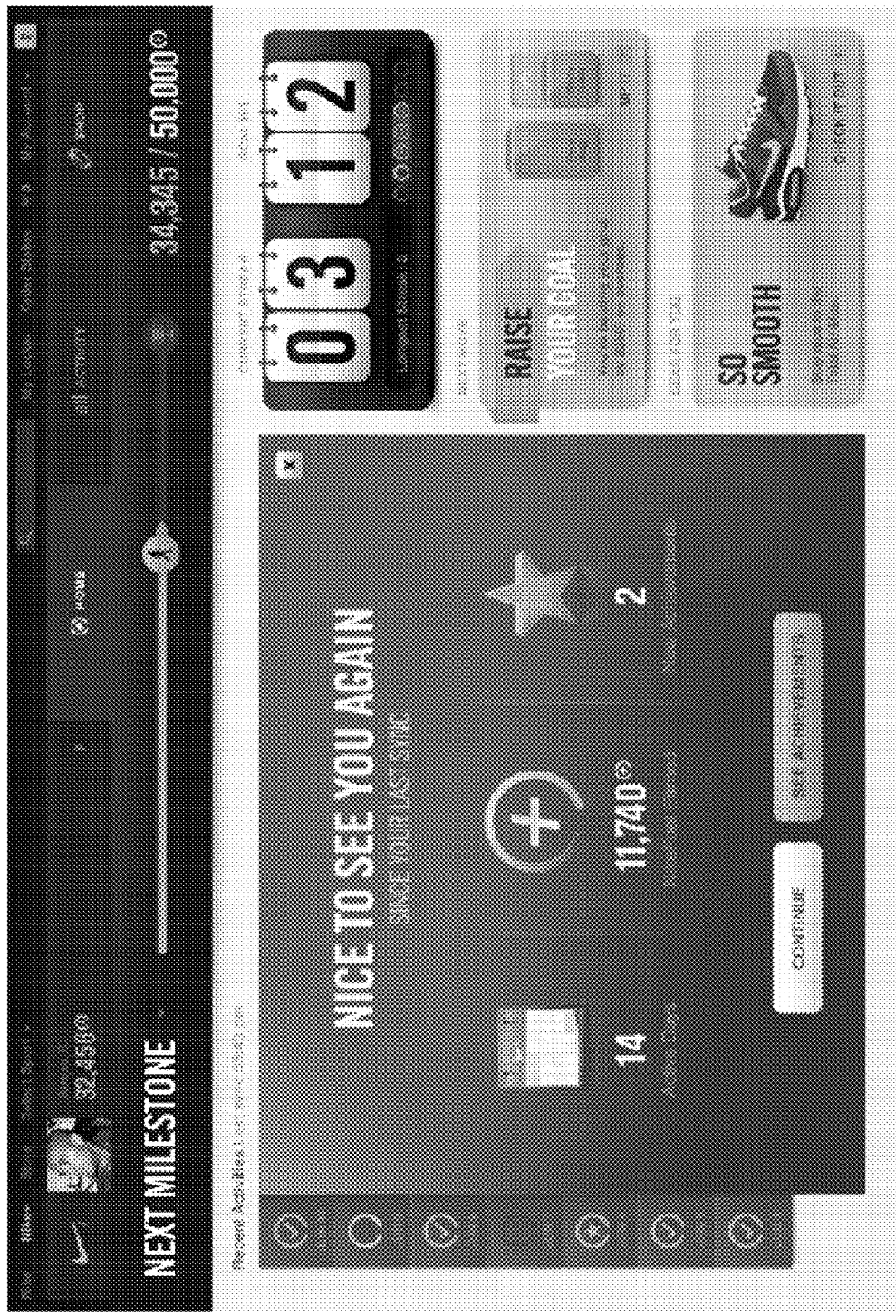

FIG. 10D illustrates an example general summary interface that is not specific to any particular goal time period. The general summary interface may provide information regarding a recent predefined time period such as a most recent week, month, year, a time period since a last synchronization with a monitoring device or a particular monitoring device and the like. The general summary interface may indicate a number of achievements reached, an amount of activity points earned since the last synchronization and/or a number of active days (e.g., a number of days in which a threshold level of activity was reached).

Figure 10E:
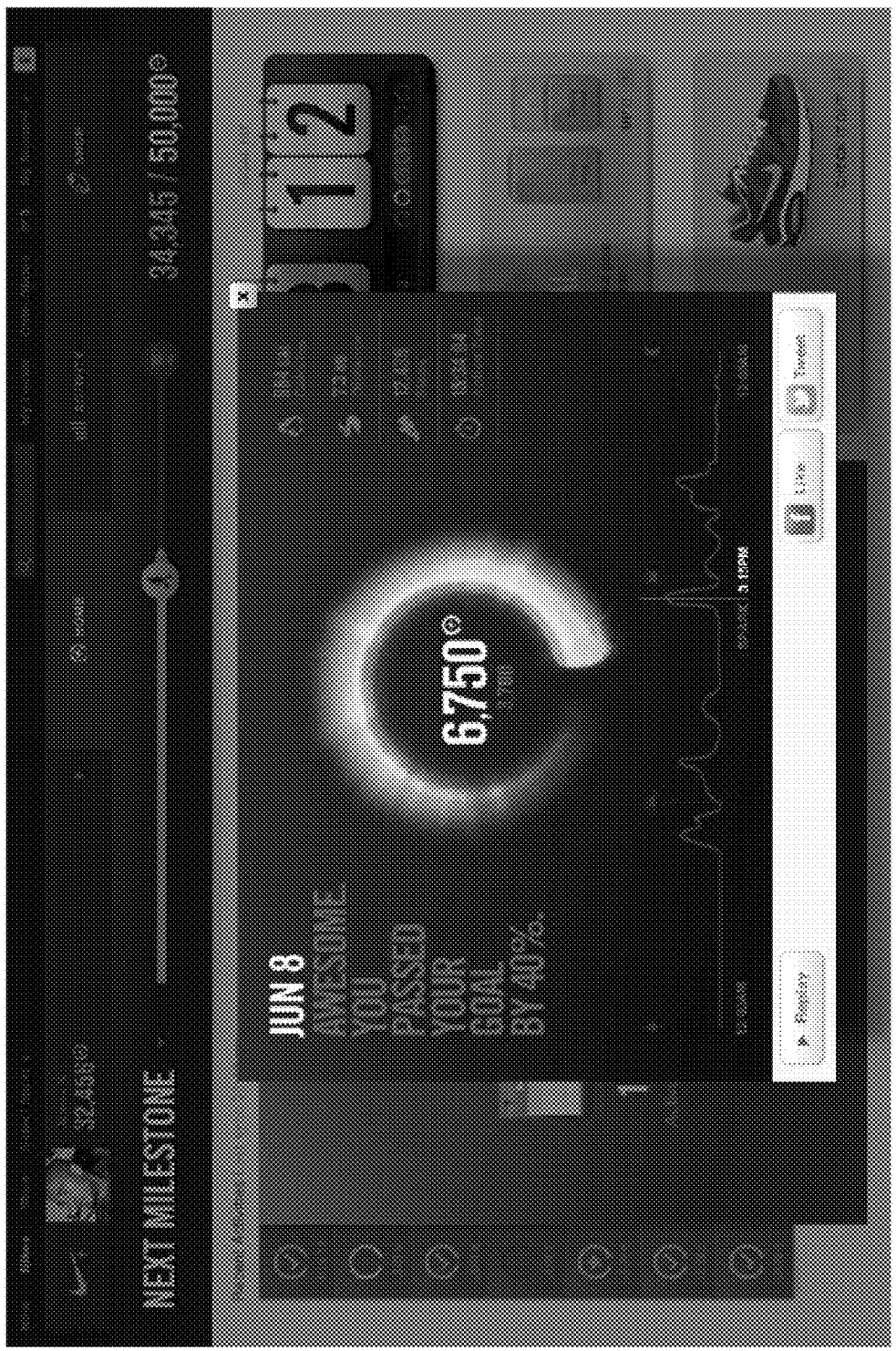

FIG. 10E illustrates an achievement celebration, where the achievement corresponds to exceeding a goal by 40%.

Figure 10F:

FIG. 10F illustrates an interface through which a user may specify a subjective feeling they had toward or during the activity time period or activity session. The user may select/specify an emoticon and/or provide user-specified comments or notes regarding that time period. This information may then be stored in association with the goal time period, activity session, and/or the user's account. In other examples, activity sessions and activity points may be tagged or otherwise labeled with location information and/or time information. Geographic location may be tagged using one or more location determination systems such as GPS, cellular triangulation, Wi-Fi location determination based on ISP and the like. Location determination systems may be internal to or integrated with the device or may be separate from the device (e.g., a mobile communication device such as a smart phone having GPS functionality). Time may be determined based on the time of the device or times of other devices, servers and systems. Accordingly, activity points and activity data in general may be filtered and viewed in a granular fashion based on geographic location and/or time.

This tagged or additional information relating to particular activity points or activity sessions may be stored as metadata in one or more examples.

Figure 10G:
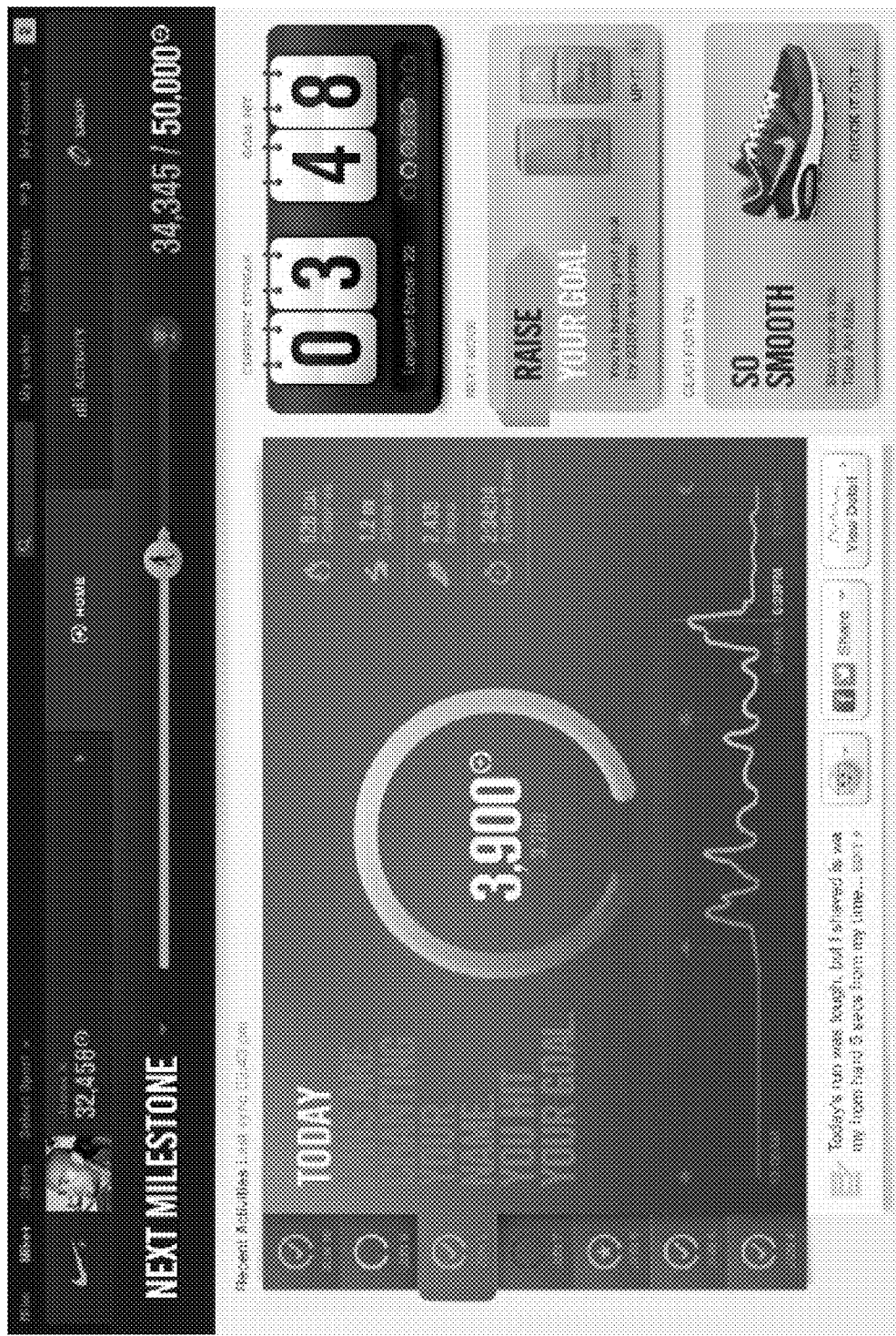

FIG. 10G illustrates an interface that may be displayed after a user has entered a user's subjective feeling and notes about the activity time period.

Figure 11A:
FIGS. 11A, 11B and 11D illustrate example interfaces providing a graph of activity performed for a period of time such as a goal time period according to one or more aspects described herein.
Figure 11B:

FIGS. 11A and 11B illustrate example interfaces providing a detailed graph of activity performed for a period of time such as a goal time period. A user may hover over or otherwise interact with portions (e.g., any portion or specific portions) of the graph to obtain activity metrics and information specific to the particular point in time or of the graph. Indicators may be provided on the graph to indicate various events such as a point at which the user hit the goal and a peak activity level. For example, FIG. 11D illustrates an indicator identifying a time period such as an hour in which the user was most active. If the goal time period displayed corresponds to a best day, a banner or other indicator may also be displayed in the detailed interface. A best day or best activity time period may be defined as a day or other time period during which a highest amount of activity points was earned, a metric reached an all-time high (e.g., a pace, distance, etc.), a user was active for a greatest amount of time (e.g., most active hours) and the like. A portion of the interfaces may also display a comparison of the current time period against other time periods.

Figure 11C:
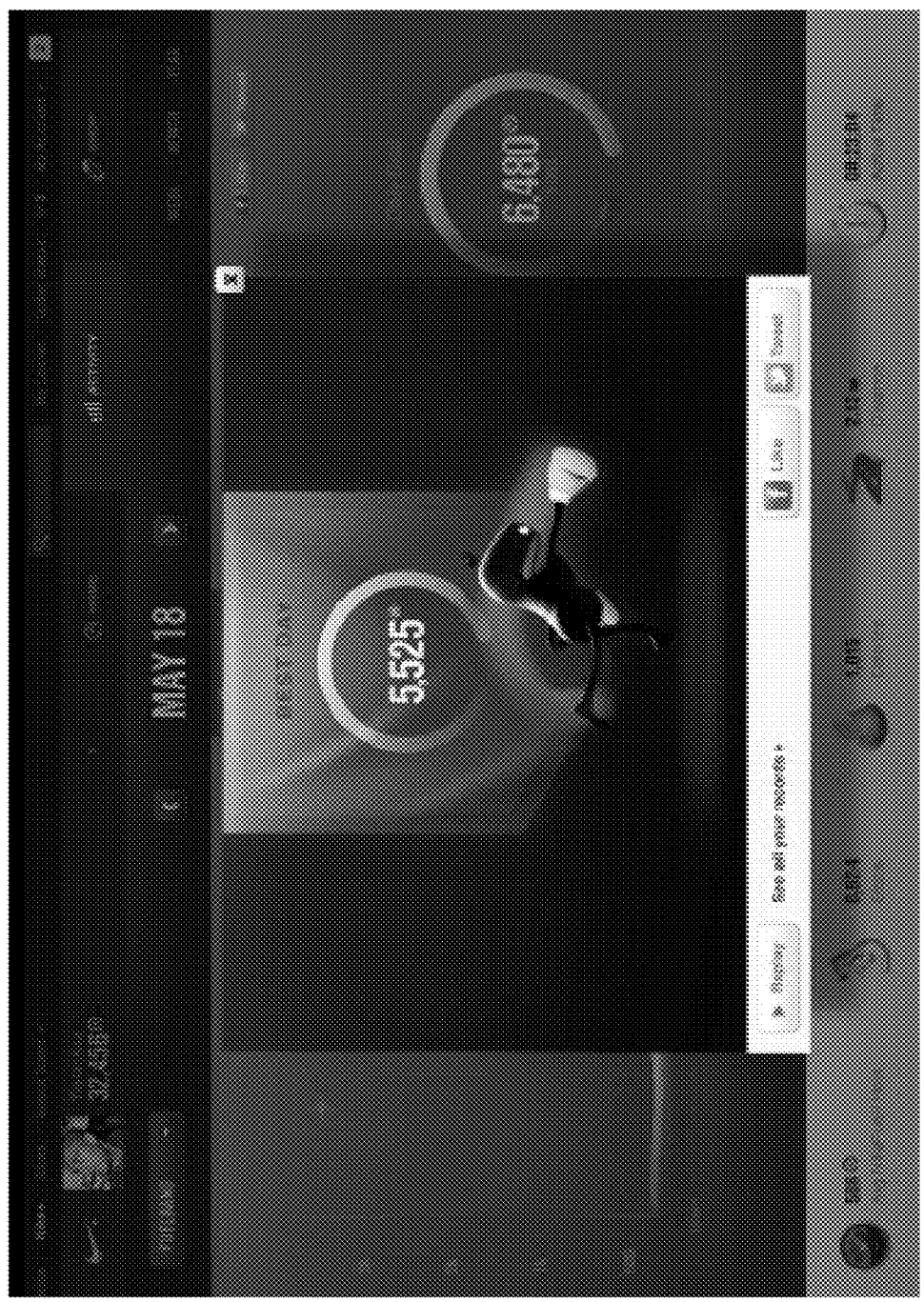
FIG. 11C illustrate an example interface identifying a best day or time period for a user according to one or more aspects described herein.
Figure 11D:
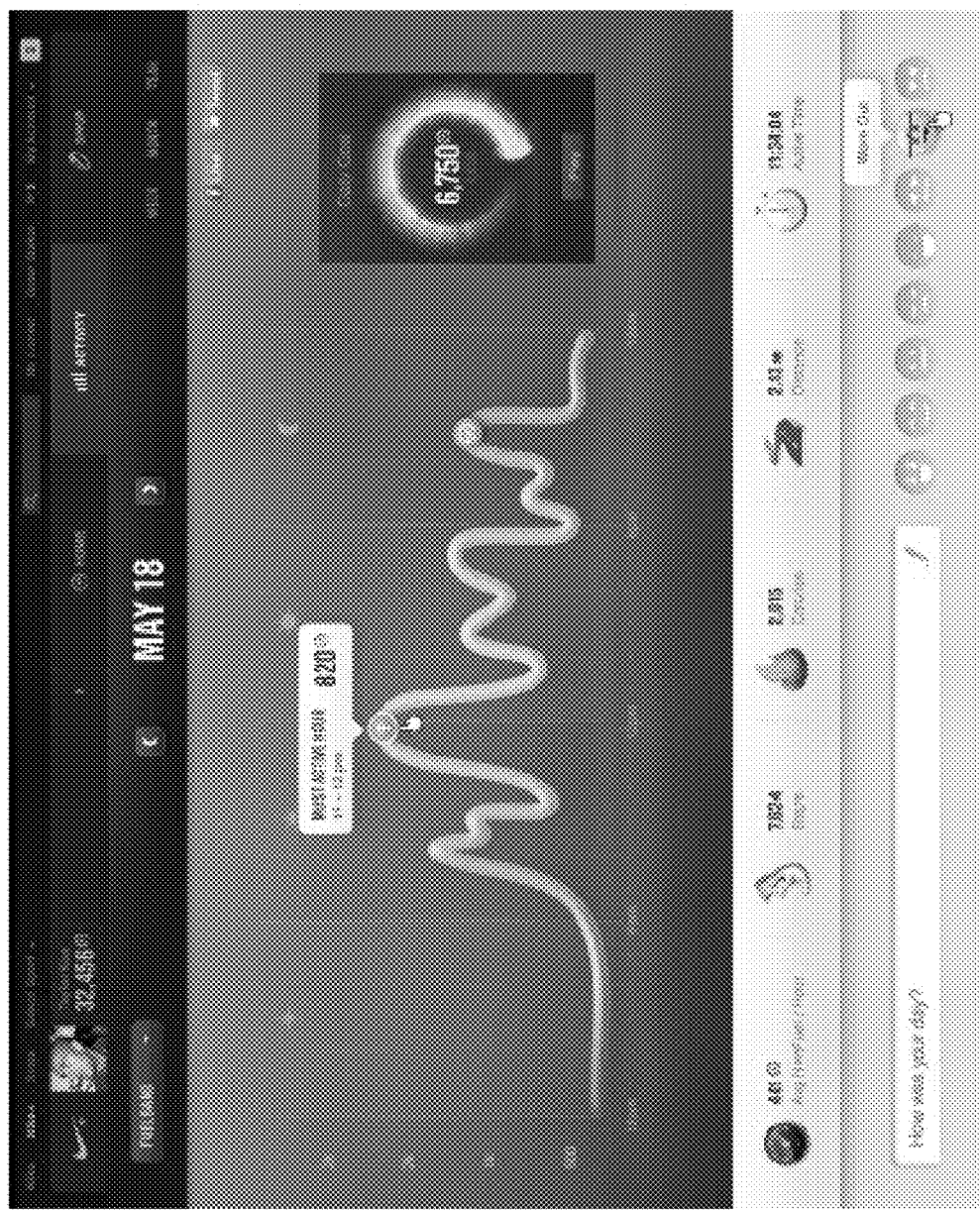

FIG. 11C illustrates a best day indication interface.

Figure 12:
FIG. 12 illustrates an interface in which a user's activity over a time period may be replayed according to one or more aspects described herein.

FIG. 12 illustrates an interface in which a user's activity over a time period may be replayed. For example, the graph may be animated such that the user's activity is graphed in animation fashion over the goal time period.

In some examples, the interfaces may display activity levels along with a breakdown of types of activities and types of monitoring devices that contributed to the accumulated activity. For example, hovering over or otherwise interacting with a graph of activity points may display a list of activity types, activity sessions, device types and the like that are associated with the activity points accumulated. The list of activity types, activity sessions and/or device types may further include an indication of an amount of activity points accumulated for each of those various parameters. The user may also filter data displayed in an activity point graph by the above noted parameters. For example, the graph may be filtered such that only activity points accumulated from a particular type of activity is displayed. In another example, the graph may be filtered such that only activity points accumulated using a particular type of monitoring device is displayed in the graph. In yet another example, the graph may be filtered such that only activity points accumulated during a particular activity session are shown. In still other examples, activity data and activity points may be associated with specific monitoring devices. Thus, a user may be able to differentiate between activities performed and activity points accumulated based on the device that was specifically used. Additionally or alternatively, the activity points corresponding to the different types of activities, different types of monitoring devices and/or different activity sessions may be displayed with different appearances in the graph. For example, accumulated activity points for a first type of activity may be displayed in red while activity points accumulated for a second type of activity may be displayed in yellow and so on. In a particular example, the different activity types may be included in the same bar graph or line graph, but each portion corresponding to a different activity type may be displayed with a different appearance. Various other visual configurations may be employed and may be user specified.

Figure 13A:
FIGS. 13A, 13B, 13C and 13D illustrate example summary interfaces displaying a user's activity levels over a week, month and year, respectively, according to one or more aspects described herein.
Figure 13B:
Figure 13C:
Figure 13D:

FIGS. 13A, 13B and 13C illustrate example summary interfaces displaying a user's activity levels over a week, month and year, respectively. FIG. 13D illustrates another example monthly summary interface. Each of the interfaces in FIGS. 13A-13D may display the user's activity level of those time periods with a further breakdown based on a smaller time frame. For example, a weekly summary may include daily bar graphs while a monthly summary may include weekly bar graphs. Interacting with (e.g., hovering over) one or more of the entries may display more specific activity information and details including metrics, types of devices used, activity sessions, types of activities performed and the like and/or combinations thereof. The interfaces may also display a goal completion rate for that summary time period. For example, in the weekly summary of FIG. 13A, the interface may display a number of daily goals hit and/or a percentage of goals reached.

Figure 14A:
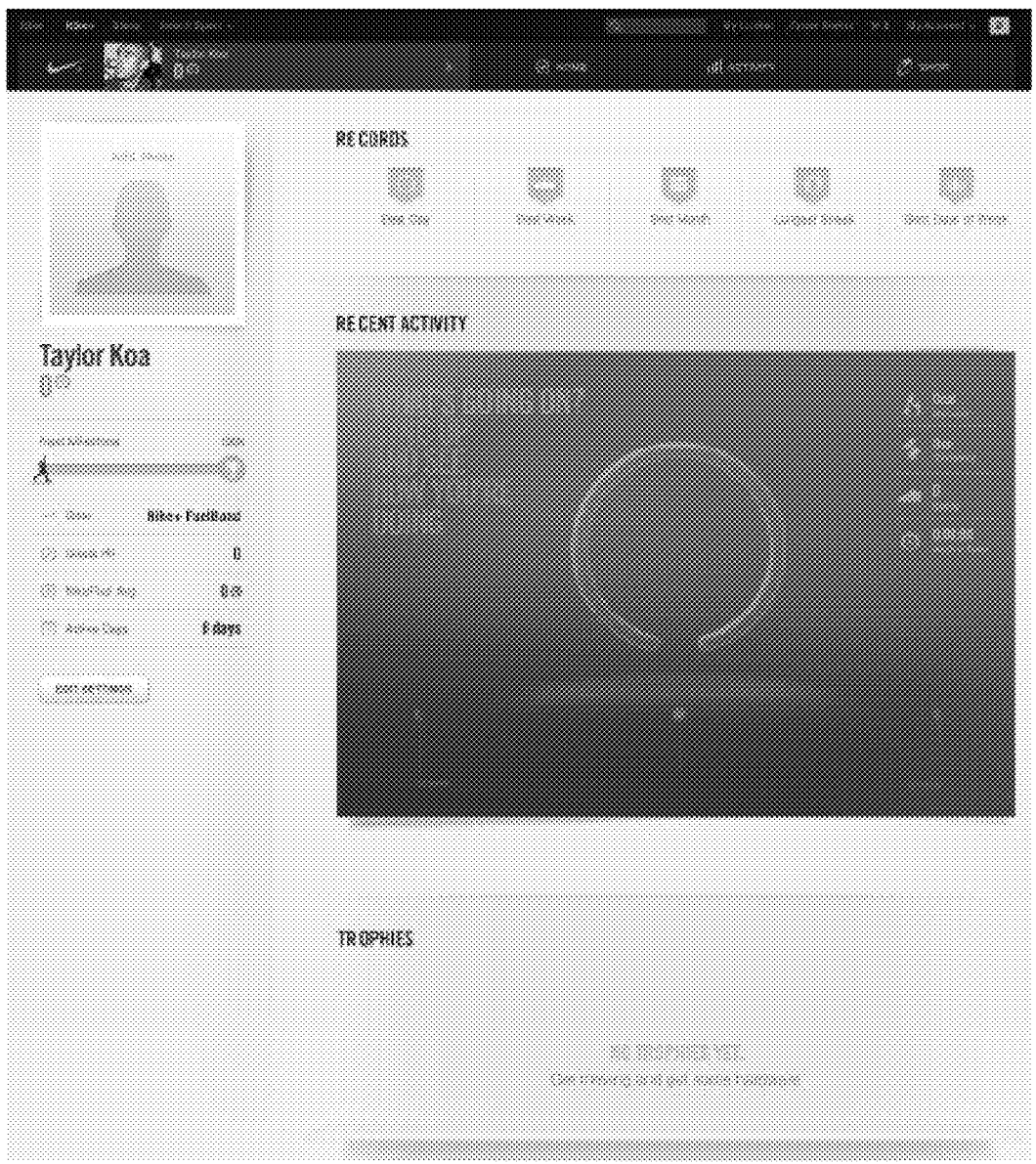
FIGS. 14A-14D illustrate example user profile pages according to one or more aspects described herein.
Figure 14B:
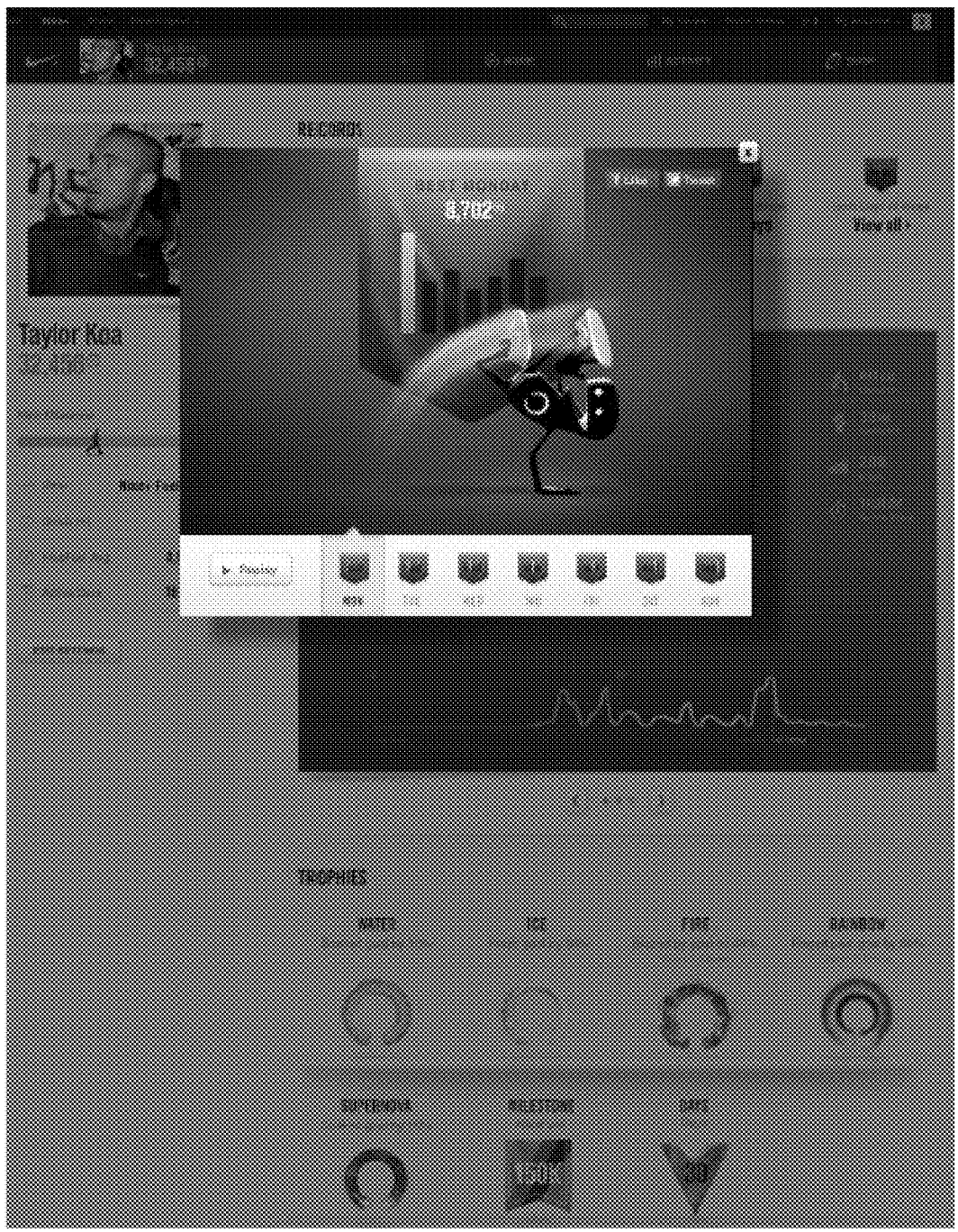
Figure 14C:
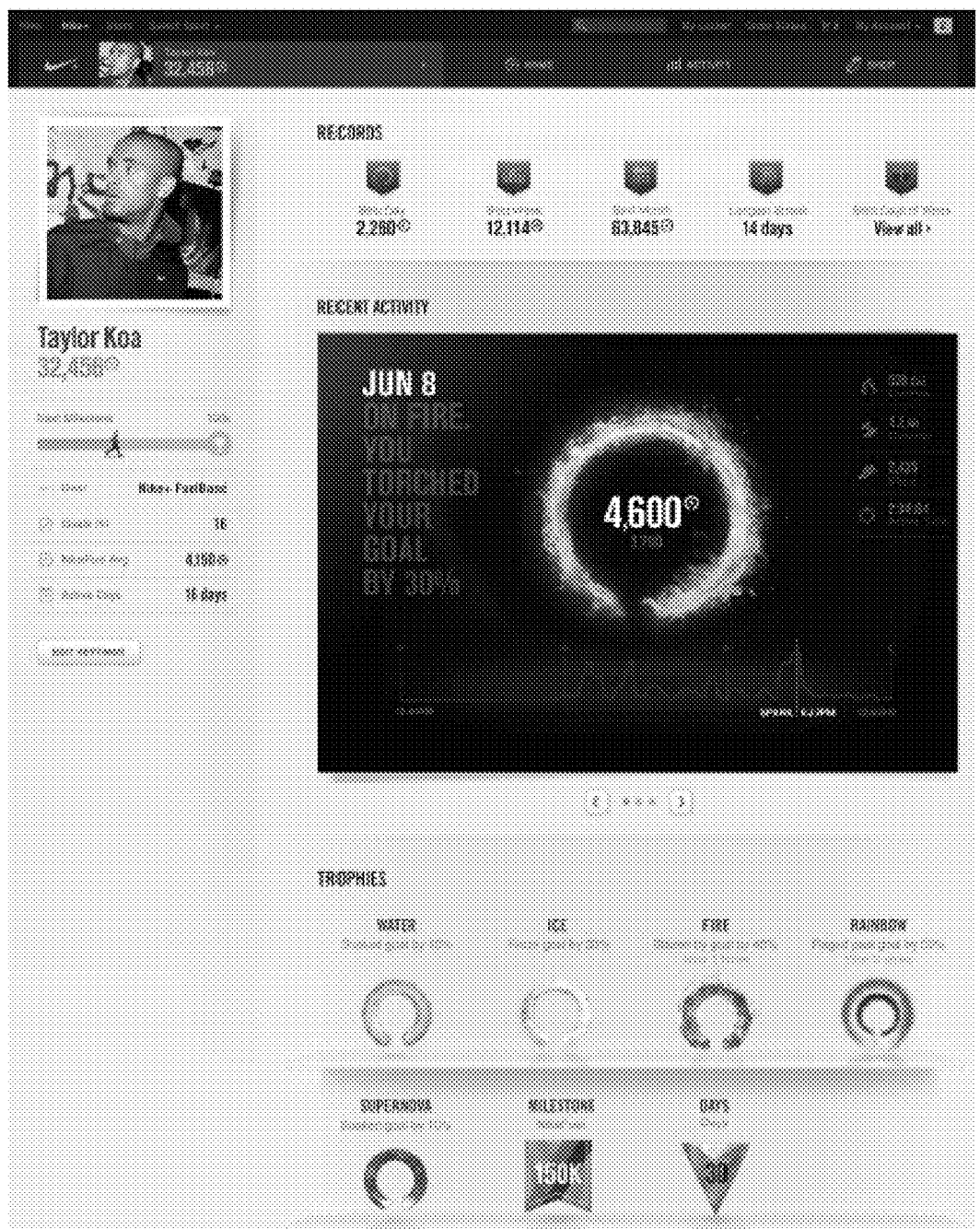
Figure 14D:
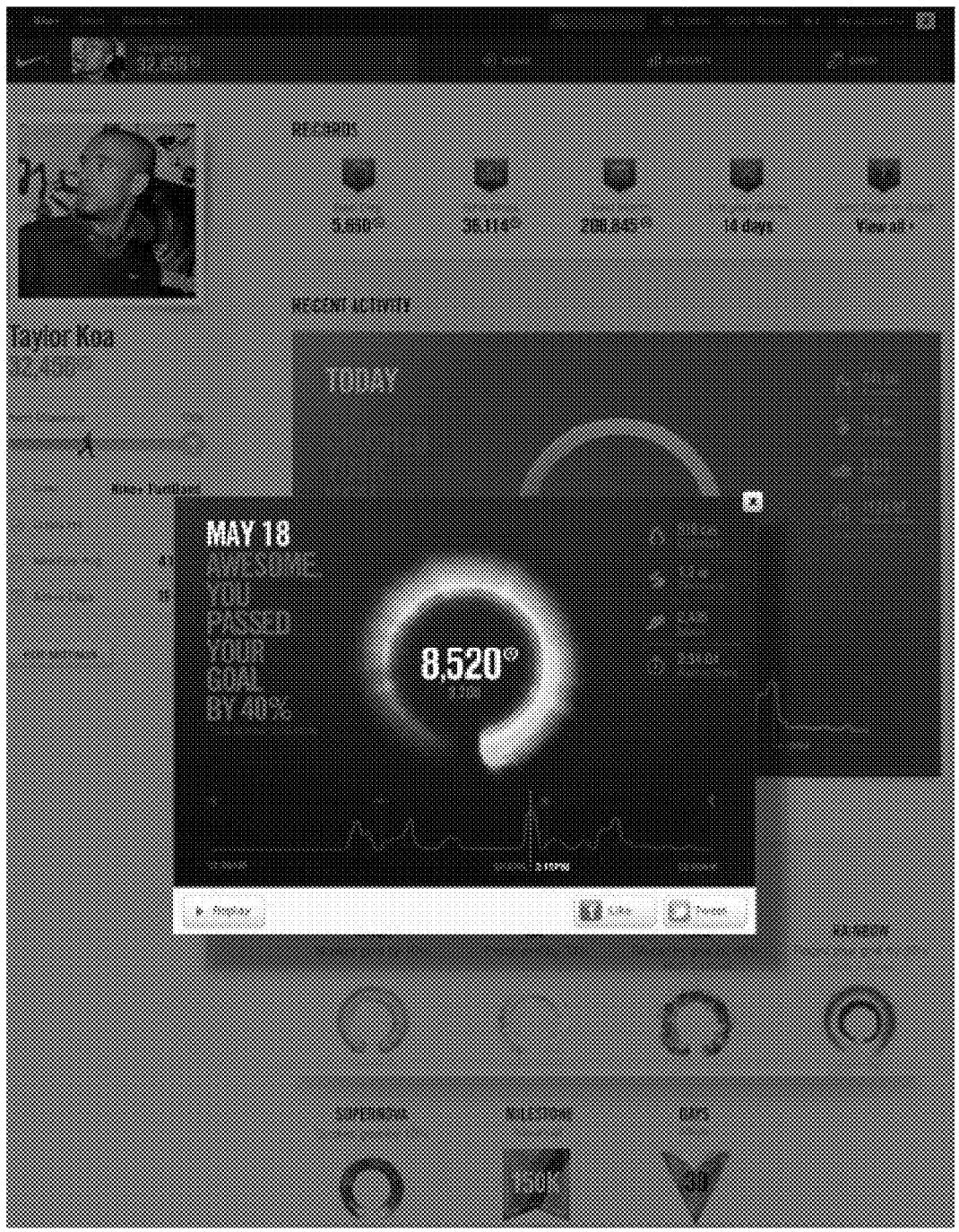

FIGS. 14A-14D illustrate example profile pages for a user. The user's profile page may include a listing of records, recent activity, achievements, milestones, awards and the like. Additionally, the user's profile may provide summary information for the user including a device most used or device type most used, a type of activity most frequently performed, activity point averages, other average metrics, personal information (e.g., name, age, location, birthdate, etc.) and the like. FIG. 14A illustrates a profile interface that may be displayed when the user has not registered or synchronized any activity data. In some arrangements, the user's profile page may also display devices and/or types of devices the user uses for recording activity.

Figure 15:
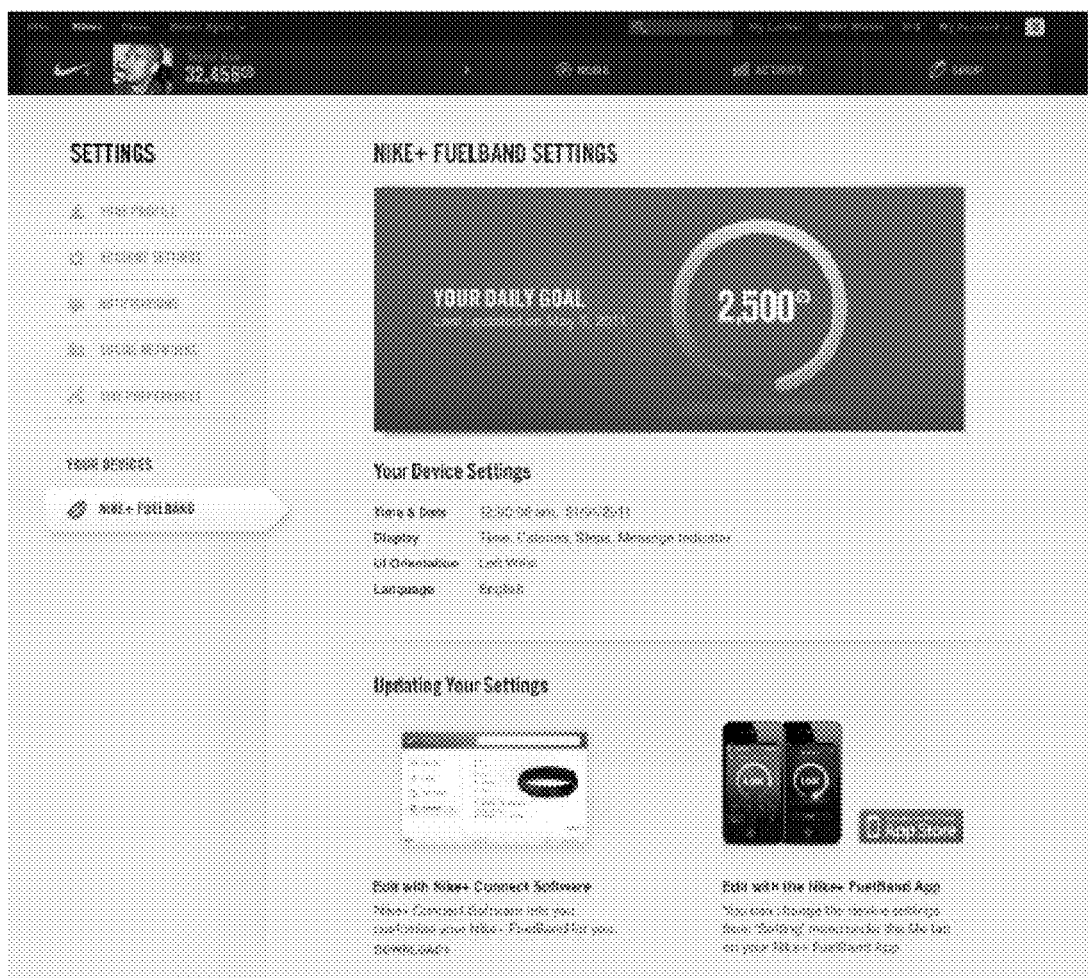
FIG. 15 illustrates an example device setting interface according to one or more aspects described herein.

FIG. 15 illustrates an example device setting interface. Each device registered for the user may have a different device setting interface on the on-line site. The device setting interface may display information about settings registered in the device such as a current time and date recognized by the device, types of data (e.g., metrics) to be displayed on the device, an orientation of the device (e.g., a wrist or other location on which the device is worn) and a language setting. In some examples, the interface may allow the user to edit or update settings on the device. The interfaces for the different devices may include different setting parameters and information. For example, an interface for a first device may include GPS settings while an interface for a second device might not include GPS settings if the second device does not include a GPS sensor. The device-specific interfaces may also include activity data and summaries (as described herein) for activities detected using the corresponding device. Accordingly, these sub-interfaces may allow a user to display activity of the user at a more granular level. In some arrangements, an on-line site or community may further identify a type of device or a specific device most frequently used by the user to record activity data or a device or type of device with which a user has recorded a most amount of activity.

Figure 16A:
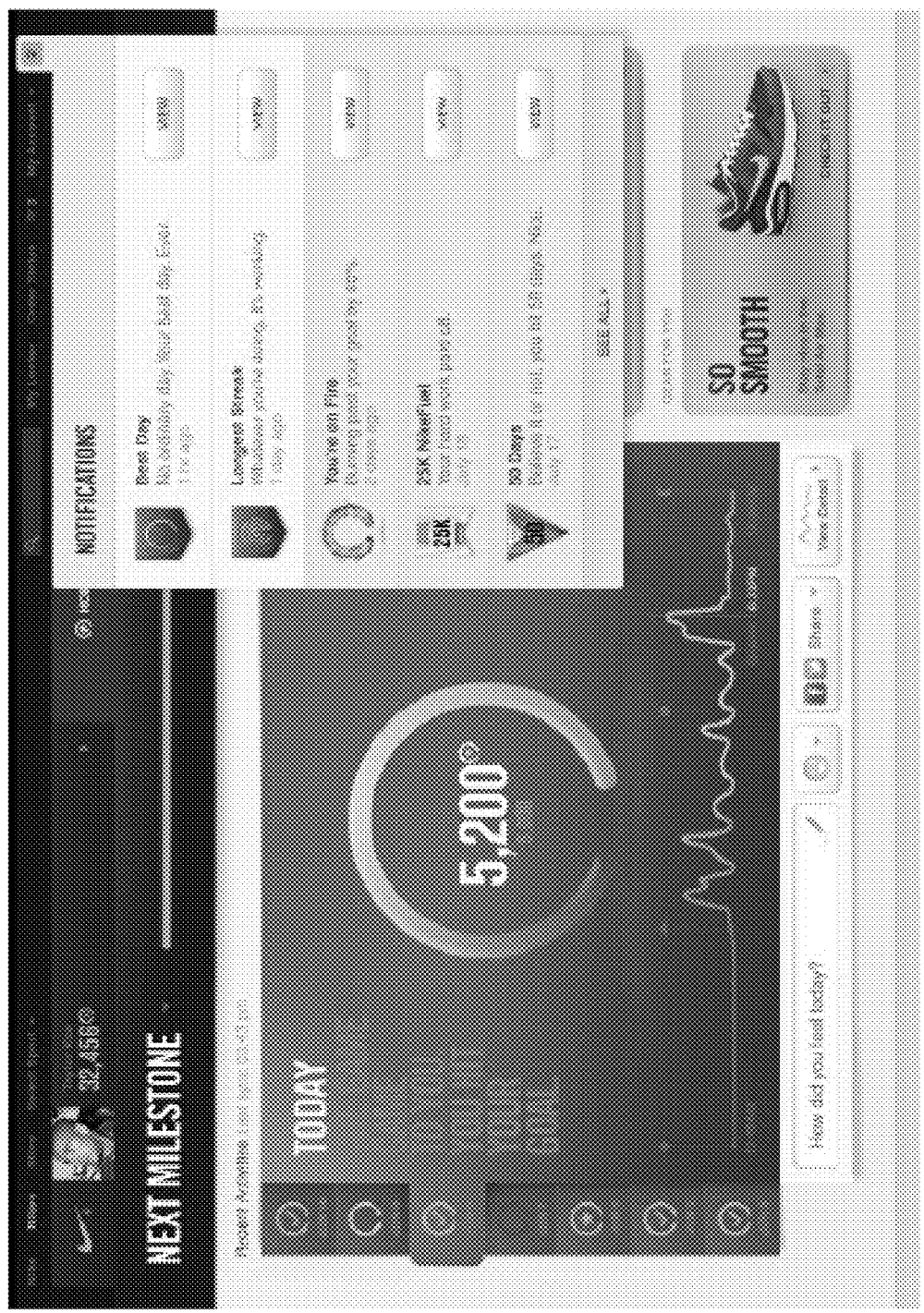
FIGS. 16A and 16B illustrate example notifications that may be displayed to a user through an on-line activity tracking site according to one or more aspects described herein.
Figure 16B:
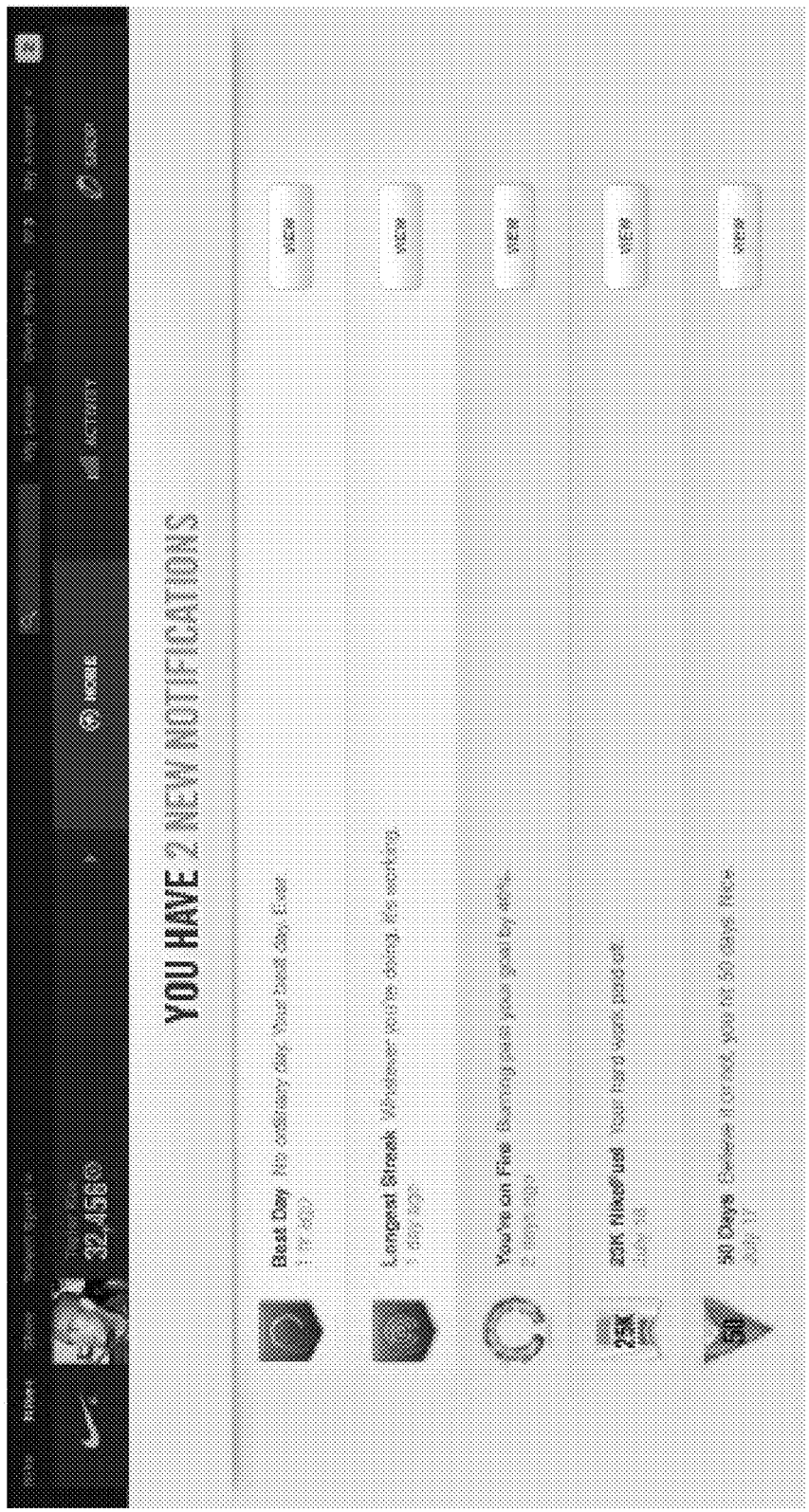

FIGS. 16A and 16B illustrates example notifications that may be displayed to a user through an on-line activity tracking site.

Figure 17A:
FIGS. 17A-17D illustrate example interface for sharing activity data according to one or more aspects described herein.

FIGS. 17A-17D illustrate example interface for sharing activity data. In FIG. 17A, for example, a user's profile may be populated with information about other users. For example, a notification or news event may be posted to the user's profile to alert the user of the other user's recent activity or activity event. For example, the other user may have recently completed a goal or reached a milestone. Such events may be displayed to the user to act as motivation and to encourage the user to congratulate the other user. Activity sharing may be configured on or off. Other sharing parameters may be defined as well. For example, a user may identify users and/or groups to which activity should be shared. In other examples, a user may define times during which sharing is allowed and/or types of events or activities that may be shared. In a particular example, a user may specify that events or activity data resulting from a first type of device, a first type of activity or a particular activity session is to be shared while events and/or activity data resulting from a second type of device, a second type of activity or another specific activity session is not to be shared. Thus, the use of the multi-activity platform allows a system to provide more granular control in sharing activity information. Activity may be shared through the user's profile (e.g., when other user's view the user's profile) or as part of other user's profile, activity feeds and the like. For example, activity events and information of a first user may be pushed to a profile or page of another user.

Figure 17B:
Figure 17C:
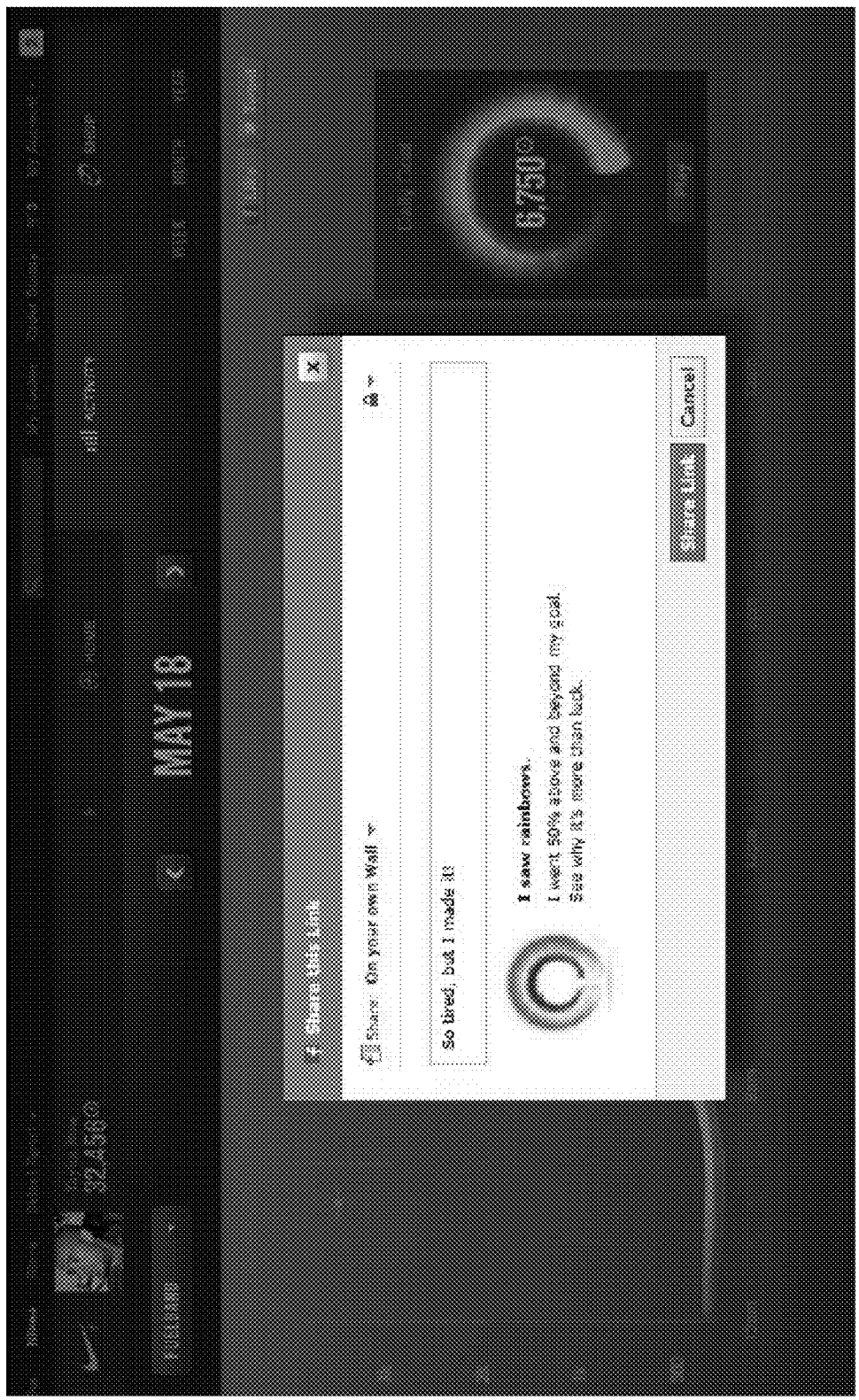
Figure 17D:
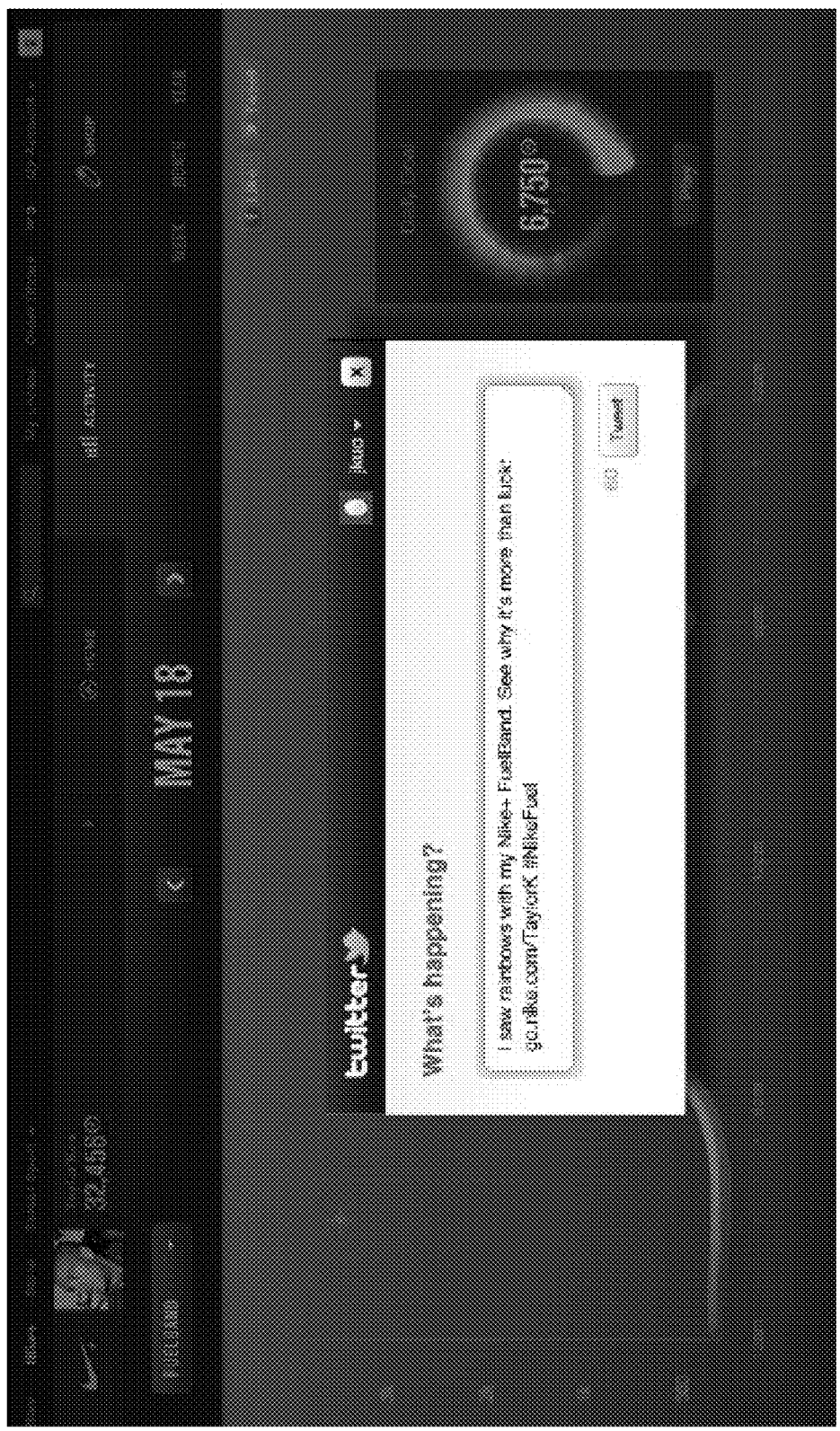

FIGS. 17B-17D illustrate example interfaces for sharing activity information and events through external social community and networking sites. FIG. 17B illustrates an interface including options for sharing on FACEBOOK or TWITTER. FIGS. 17C and 17D illustrate pop-up interfaces through which a user may submit a note, specify activity information to be shared, identify users to which the information is to be shared, and the like. As with configuration information that is and is not to be shared, the user may configure sharing of information through external sites and systems based on device type, activity type, activity session and the like as well. In one example, the user may configure sharing of information through external sites and systems separately from sharing through internal systems or communities.

Multi-Activity Application/Device Interface

Interaction between activity monitoring devices, activity tracking services and systems, intermediary devices and other computing devices or systems and/or applications executing thereon may be conducted using a shared application protocol interface (API). For example, applications executing on a smart phone may use the API to retrieve data from and transmit data to activity monitoring devices adopting the API. Similarly, communications between an activity monitoring device and an activity tracking service or system may be conducted using the API. Communications between dedicated activity monitoring devices may also be conducted using the shared API. The use of such an API allows for interoperability between devices of different types and activity data of different types. An example of the protocol is described in further detail below.

Activity Data Tracking and Processing

The API for activity data tracking and processing may include a variety of functions including activity deletion, activity detail requests for one or more activities, activity listing requests, activity summary retrieval, posting and deleting tags, requesting activity type-specific information, requesting activity data based on date ranges and the like. The API may be used for monitoring devices and other devices to interact with a multi-activity system as well as for the multi-activity system or other computing devices to retrieve information from and transmit information to the monitoring devices.

Activity Delete: This service/interface may be used to delete an activity (e.g., an activity session having a particular activity session identifier). Once deleted, a user will no longer be able to view this activity, and it might no longer be used for any calculations, aggregations or challenges. For example, a number of activity points awarded for the activity may be deducted from a total activity point amount upon deletion. Alternatively or additionally, the activity delete function may be activity type-specific. Accordingly, an activity delete command may cause all activity data for a particular type of activity to be deleted.

Activity Detail: Devices may also be able to retrieve detail on a single activity or activity session or by activity-type. This service returns all the information related to a specific activity using the activity ID as parameter or activity type and/or a list of activity sessions of an activity type using type specifications. Details may include raw sensor data, metrics, location information, participating individuals and the like.

Activity Detail for the Last Activity: This service returns information related to the last activity session. Accordingly, instead of having to be aware of the ID of the last activity session, the system may provide a function call that is particular to the most recent activity. The user may also specify an activity type, thus allowing a device to select a last activity session for a particular activity type. Similarly, other types of parameters may be used to further or differently distinguish between last activity sessions.

Activity List: Return a list of the user's activities. This service is useful for any application wishing to obtain a list of activities by date, time or index. For example, a device may request all activities performed between two particular dates or times. The list may further be filtered based on other parameters including activity types, device type, device ID, activity characteristics (e.g., above or below a threshold pace, a particular weather condition, a particular terrain or location, activity equipment used etc.) and the like. Retrieval using indices may refer to specifying an activity ID range and retrieving all activities within that ID range.

Activity Summary for the Specified Month: This function allows a device to retrieve a user's activity summary for a specified month. The activity summary may include statistics regarding a number of goals met, an average number of activity points earned (or other activity metric), identification of streaks of goal completion and the like, as is described in further detail below.

Activity Summary for the Specified Week: Get a user's activity summary for a week.

Activity Summary for the Specified Year: Get a user's activity summary for a specified year.

Activity Update: This service returns all the information related to a specific activity using the activity Id as a parameter. In some examples, this function may include a date or time parameter specifying a last time when information relating to the specific activity was retrieved. The device or system from which this information is requested may then transmit all information that is new as of the specified date or time.

Basketball Activity Detail: As described, activity data requests may be activity type specific. Accordingly, an activity type specific function may be provided to retrieve details on a single basketball activity session. This service returns all the information related to a specific activity using the activity Id as parameter.

Basketball Activity List: Return a list of the user's basketball activities.

Customized Tags: Adds user customized tags for specified user. For example, a user may be allowed to define customized characteristic tags for activity sessions. Tags may include, weather, equipment, terrain, food eaten prior to the activity session, user-specified notes and the like.

Daily Activity Point Summary Service: Gets a user's daily activity point history over an interval. For example, a time period such as 9 AM-12 PM or 9 AM-6 PM may be specified and data for that time period may be retrieved for each day. Alternatively or additionally, different activity point periods may be defined for retrieval such as a weekly activity point history or an hourly activity point history.

Delete Tags: Deletes the user tags for a specified activity.

Extended Metrics: Adds user extended metrics for specified activity or gets a list of the extended metrics associated with the activity Id or deletes a list of the extended metrics. Extended metrics may refer to metrics that are not automatically synchronized. In other examples, extended metrics may refer to any metrics that are user entered/specified (e.g., not automatically detected or generated by an activity tracking device or monitoring system).

Get Datastreams for Start and End Time: Get datastreams for a start time and an end time. This service returns all the datastream information related to the user between the designated start and end time parameters. For example, the datastream may include activity data and information as well as other actions taken by the user such as updating of a profile, adding a friend, setting a goal and the like. Accordingly, this function allows for retrieval of data beyond recorded athletic activity data and may include all actions taken with a particular device to which the command is being sent.

Get Tags: Gets the user tags for specified activity session. In one example, this function may enable a device to retrieve the values for various tags within activity data. In some arrangements, various sets of tags may be defined for different activity types (or for different device types). Accordingly, upon determining the tags that are associated with an activity type or device type, the system may retrieve or extract values for those tags from the activity data Get User Events: Return list of user events to be displayed. User events may refer to actions taken by the user or achievements/goals reached.

Post Tags: Adds the user tags for specified activity. Accordingly, a user may tag activity data stored on one device via a second, physically separate (and potentially remotely located) device.

Post Tags By Date Range: Tags all the activity sessions in the specified date range with one or more specified tags. Tags may relate to a user's subject feeling, weather conditions, terrain, equipment used and the like. In some examples, the function may also be configured to automatically calculate the values for tags associated with the activity type and store those values in association with the tags for the activity session or activity data.

Running Activity Detail: This service returns all the information related to a running activity using the activity ID as parameter.

Running: My Activities: Returns a list of sport activities for running and their aggregations.

Running: My Activities v1.0: Returns activity report, activity history details and lifetime details for a user for running activities.

Running: My Activity: Returns a sport activity by activity id for a user.

Training Activity Detail: Get detail on a single activity. This service returns all the information related to a specific activity using the activity Id as parameter.

Training Activity List: Return a list of the user's activities summary for a training-type activity.

Challenges

Challenges may be issued and conducted between two users using two different devices and device types. The following provides a list of APIs that may be used to create, track and complete a challenge.

Accept Challenge: Accept a challenge.

Accept or Deny Challenge: Accept or Deny challenge will be a user's response once they have been invited to a challenge.

Add Challenge: Add a challenge with the supplied information such as an objective, a duration, participants, whether the challenge is public or private, location, name of the challenge, start time and the like. In some instances, the add challenge service allows a user to specify a predefined challenge type such as Create Daily Goal, Challenge of the Week, Head to Head, Group Fuel Goal, Group Workout, Drill Based Challenge and Team Up, as described in further detail herein. Privacy levels may also be set. For example, the following table describes example privacy levels.

| Id | Description |
|---|---|
| 0 | Private. You can only join if invited by the challenge creator. Only the participants can view the results of the challenge. |
| 1 | Participants and friends of creator can view. Does not appear on searches. (Note: As the concept of friends does not exist right now on MSP, 0 and 1 are the same.) |
| 2 | Public. Appears on searches. Anybody can view the challenge details and leader board, but not join. |
| 3 | Public. Appears on searches. Anybody can join, view the challenge details and leader board. |

Create or Update Challenge: Using this service, different types of challenges can be created/updated. The business rules and required parameters depend on the type of the challenge being created. The challenge types are: Create Daily Goal, Challenge of the Week, Head to Head, Group Fuel Goal, Group Workout, Drill Based Challenge and Team Up.

Challenge of the Week: Creates a challenge of a type that can only be created once a week. The challenge of the week may include various rewards that are specific to this type of challenge.

Create or Update Daily Goal: This service is used to create/update the daily goal for a specified date. If the date supplied is today, the daily goal for today will be changed/updated. If the date supplied is any date in the future, the future daily goal value will be changed. An error will be returned if the date supplied is prior to today.

Drill Based Challenge: Challenges can be created based on a drill. This form of the service will look up the details of an existing drill and create a challenge matching the parameters of the drill. Drills may refer to a predefined sequence of physical movements at specified times. Groups may or may not be supported. The overview of this Head to Head challenge is of a non-competitive variety. A challenge of this type indicates that the creator of the challenge invites her/his friends to beat their challenge. Whether the participants beat the challenge or not, the result is sent to back to original challenge poster. That is, the participants performance are not compared with one another and is, instead, compared to the objective. Thus, multiple participants may beat the challenge.

Get Challenge Details: Gets all the details of a challenge and the associated leaderboard (e.g., a listing of participants and a current level of performance/progress). In some arrangements, this function may check whether the logged-in user has permissions to see the requested challenge details.

Get Challenge List 1.0: Get a list of the challenges past and present on which a specific user has participated either as creator or as member. The list may be ordered by the end date of the challenge with the most recent challenge listed first. This service also lists goals, which is a type of challenge (me vs me) where there are no challenge members (other than the creator/user) or leaderboard.

Get Daily Goal List: Get a list of daily goals across multiple dates for the given user.

Group Activity Point Goal: The group activity point goal is a challenge type, which is individual based (but in a team), and non-competitive. A challenge of this type involves a creator of the challenge inviting her/his friends to join in the challenge and the sum of the activity points of all of the members/participants should be larger than a predetermined amount at the end of the challenge. There may be several business rules for this challenge type. For example:

1) A user can have up to 5 challenges of this type, including created challenges and accepted challenges, e.g., if a user has already created 5 challenges, the user cannot accept other challenges.

2) Each challenge of this type may hold up to 5 users (excluding the creator), i.e., the creator of a challenge can specify at the maximum 5 friends to send invitations to.

3) Challenges of this type may always be 7 days long.

4) After a challenge ends, velocity can make a call to create a new challenge with the same parameters.

5) The invitation can be accepted at any time within the 7 days, the amount of fuel earned since the start time will be credited to the challenge.

6) A challenge is not expected to be changed after it is created.

Other rules, restrictions and the like may be defined and is not limited to the above example.

Group Workout: The group workout is a challenge type, which is individual based (but in a team), and non-competitive. A challenge of this type is that the creator of the challenge invites her/his friends or other participants to join in the challenge and each member in the challenge should do at least the predetermined amount of workout. There may be various business rules for this challenge type. For example:

1) A user can have up to 5 (or any other number) challenges of this type, including created challenges and accepted challenges, e.g., if a user has already created 5 (or other number) challenges, the user might not be allowed to accept other challenges.

2) Each challenge of this type can hold up to 5 users (excluding the creator), i.e., the creator of a challenge can specify at the maximum 5 friends to send invitations to.

3) Challenges of this type might always be 7 days long.

4) After a challenge ends, velocity can make a call to create a new challenge with the same parameters.

5) The invitation can be accepted at any time within the 7 days, the number of workout performed since the start time will be credited to the challenge.

6) A challenge is not expected to be changed after it is created.

Other rules, restrictions and the like may be defined and is not limited to the above example.

Head to Head: Head to Head challenges are challenges in which the participants' performances are treated individually and not grouped. The participants' performances may further be compared with one another to determine a winner.

Search Challenge: Challenge search will return a list of challenge objects based on the keyword provided. The challenge objects in the list may be a trimmed down version of the full challenge object.

Team Up: Team Up is a challenge type that may have the following rules:

1) There are at most 2 members. Other limits may be set such as 3, 5, 10, 13, 17, etc.

2) Any two (or other number of) members can have only one active team up.

3) The challenge starts when the second person (or last person) accepts.

4) The challenge ends 72 hours after the start time.

5) If the challenge hasn't started 24 hours after it is created, it expires.

6) The fuel amount is integer.

7) The challenge cannot be updated.

8) A person can have only 50 active team ups.

The Challenge Type can be:

Teamup Band Together Friend

1) The user selects a friend from the list of friends and creates a challenge.

2) The invitation is sent to the friend.

3) If the friend accepts the challenge the challenge becomes active.

4) Each member should reach the fuel target so the challenge can be considered completed.

Teamup Band Together Blind Match

1) On the blind match you select one of the preset activity point targets and proceed to create the challenge.

2) The system will match you with a random user taking the same type of challenge with the same fuel level.

3) If a match is found, the user has the right to accept or deny it.

4) If the user accepts, the start time and the end time will be updated.

5) If the user denies, both the user and the creator of the challenge are available for blind match. Basically, a separate challenge is created for the user.

Legacy API

Some services or functions may be defined to interface with legacy systems such as a legacy activity tracking and monitoring site or system.

Generate PIN Service: Retrieves a unique PIN for an empty user container.

Generate Token Service: Generates a one-time-use token with which the local software can launch a browser to a specified website or page, and automatically login the user. The token is one-time-use only as it is passed in the clear over HTTP, and therefore cannot be used to hijack a user's account.

Get PIN From Token: Get PIN from a one-time access token.

Get PIN Status Service: Provides information about the user container associated with this PIN.

Sync Complete Service: Called to tell an activity tracking application that the sync session is complete. This call may have an internal delay for 10 s in order for this call to be the last in a group of activities.

Community

The multi-activity platform and system may further host a community of users seeking to track and monitor their activity levels. Communities may refer to all users registered with the system or a sub-group within the users (e.g., a group of friends, a location based group, an organization based group, age groups, device type groups, etc.). Accordingly, various services and functions may be provided to interact with community functionality.

Get Community Challenge Stats Totals: This service will provide the lifetime aggregations for any community/challenge type pair. For example, a user may request aggregation information for challenges of the week within the 25-49 male community. The community may be defined based on demographics, activity type, device type, age group, gender, location and the like and/or combinations thereof.

Get Community Leaderboard: This service will return the requested Community Leaderboard. This service may cause the system to calculate the Leaderboard, or may only return the leaderboard if already generated/present. In one example, if the Leaderboard has not been calculated yet, an error message will be displayed. There may be multiple types of Community Leaderboards including a Seven Day Rolling and an All Time. These two types of leaderboards can be requested for each existing type of drill.

Get Community Stats: This service will provide an aggregation of existing as well as 3 new community aggregations as described below. These are example aggregations and do not represent an exhaustive list.

Community—Total/Average Fuel Today, Week, Month, Year, All Time.

Community—Average Activity Point Daily Goal for Device X users—Today Week, Month, Year, All Time.

Community—Total Device X Daily Goal Reached Today, Week, Month, Year, All Time.

Community—Total/Average Step: Today, This Week, This Month, This Year, All Time.

Community—Total/Average Calories: Today, This Week, This Month, This Year, All Time.

Community—Average Community Daily Goal.

Community—Total/Average Distance Today, This Week, This Month, This Year, All Time.

Community—Total/Average Calories: Today, This Week, This Month, This Year, All Time Community—Total # of Users for each vertical and entire community.

Get Community Stats Frequencies: This service will provide the History aggregations for any community/activity pair for any frequency (e.g., weekly, monthly, annual, etc.).

Get Community Stats Total Users: This service will provide the real time number of community users (e.g., all users on the site or within a more specific community).

Get Community Stats Totals: This service will provide the lifetime aggregations for any community/activity pair.

Get XYZ Community Leaderboard: This service will return the requested activity XYZ Community Leaderboard. Activity XYZ may correspond to a particular type of activity or activities performed using a particular type of tracking device or devices. This service may calculate the Leaderboard or might only return a leaderboard if already present. If the Leaderboard has not been calculated yet, an error message may be displayed in some examples. There are multiple types of Community Leaderboards including Current Week and All Time. These two types of leaderboards can be requested for each existing type of drill.

Get Friend Leaderboard: This service will calculate and return the requested Friend Leaderboard. There may be multiple types of leaderboard including Friend Leaderboards, Current Week and All Time. These two types of leaderboards can be requested for each existing type of aggregation.

Get Friends Leaderboard: This service will return a Leaderboard for a specified drill that ranks the user and his/her friends only. If the user doesn't have any friends the leaderboard won't be shown.

Get Friends List All: This service allows a user to see a listing of all their friends.

Get Friends List Common: This service allows a user to see a listing of friends user has in common with another friend.

Get Friends List Most Active: This service allows a user to see a listing of the recent activity of all of a user's friends.

Get Friends List Recent Activity: This service allows a user to see a listing of most recently active friends and what they did (e.g., activities performed, devices used, locations, etc.).

Get Friends List Team Up: This service allows a user to see a listing of friends user most recently did a team up with.

Get Activity Point Friends List Service: Returns a list of the user's friends with corresponding information on their activity points (cumulative level, daily level, daily goal.) The request specifies sorting by activity, cumulative activity point level, daily activity point level, or screen name. This service is used by applications to get a list of friends with corresponding activity point levels for a user.

Get Homepage Community Stats: Returns an object representing cumulative stats over a rolling 30 day period for the given activity type and community type.

Social Share: FACEBOOK: Post/Share content to FACEBOOK that friends can see.

Social Share: TWITTER: Post/Share content to TWITTER that friends can see.

Test end point—Trigger Community Leader board calculations: This end point is used for testing purposes to trigger the calculation of Community leaderboards. This is an asynchronous call which will always return a success message. This end point will not be mapped by APOGEE and will only be available on the staging environment. There are two types of Community Leaderboards, Seven Day Rolling and All Time. These two types of leaderboards are calculated for each existing type of drill.

Device

Different devices may have different setting or setup parameters and procedures and ways in which data is to be communicated and/or stored. Accordingly, APIs may be provided for a device to retrieve needed data and/or to submit various types of information.

Device Settings: (GET) Retrieves a user's preferences for a specific device. (POST) Updates a preference for the specified User Device. UUID represents the user device id.

Device Settings (Protocol X): Sets device settings to a particular protocol such as protocol X.

Device Setup: Explanation on how devices are implemented.

When syncing a device, a device may be required to have a serial number and type. If either of these items is not present or incorrect, the application may provide an error. If you are associating a group of devices to a user that have been synced together, then you must pass the DeviceConfigGroupId that was presented when the devices were first synced. Also if the individual device has been associated with a user, then the DeviceId may also be required to be passed. If DeviceConfigGroupId is not sent when the devices are already associated with a user as a group, then it considers them a new group of devices and assigns a new DeviceConfigGroupId.

Serial numbers are unique identifiers. If a device with a serial number that is already associated to a user is sent (without sending in the DeviceConfigGroupId or DeviceId), then the system may return an error. The error will state that this device's serial number is already associated to another user, even if you are that user.

A Type variable may be defined as the type of device that is being associated to the user. This variable or parameter may be required in order for a system to know what kind of device is being associated. If the device passed in has an invalid type or is empty then an error will be thrown.

Devices that have not been grouped together before are considered a new group of devices. If two devices that have already been associated with a user with a brand new device are grouped, this association may constitute a new device group. Because this represents a new group of device, a DeviceConfigGroupId is not required in the communication. The DeviceIds for the old devices that have already been associated with the user may be passed to the system. When the devices are synced, a new DeviceConfigGroupId and a new Device Id may be returned.

For a first sync for new devices: devices with an unused serial number may be sent to the system without a DeviceId or DeviceConfigGroupId. The DeviceConfigConfigId will be returned along with each DeviceId for each of the devices in the order that they were passed/communicated.

For any sync after the first with the same devices: the devices' DeviceIds and the DeviceConfigGroupId are transmitted/communicated. The same DeviceConfigGroupId will be returned back, but not the DeviceIds.

For any sync after the first sync with new devices along with old devices: DeviceIds for the old devices are communicated without DeviceIds for new devices. In some arrangements, a DeviceConfigGroupId might not be sent since this will be a new group of devices. The new DeviceConfigGroupId will be returned to be used for future syncs of these devices. The DeviceId's of the new devices will be returned also.

Phone Device Settings (Protocol X): Sets Phone device settings to a particular protocol such as protocol X. This may also allow the device to know what protocol is to be used to communicate with the multi-activity platform.

Reset Device: Sets the User Device "delete_ind" flag to true. UUID represents the device id.

Reset LastSyncOffset and LastSyncTimestamp: Sets the device's LastSyncOffset and LastSyncTimestamp to the given values.

Retrieve, Add or Update Device: (GET) Retrieves a user device record or records. (POST/PUT) Adds or updates a user device record. UUID represents the user device id, returned in both the POST and the PUT response body.

Fitness/Workout Programs

Activity data recorded during a user's performance of a fitness or workout program may be communicated in accordance with various predefined functions and services.

Fitness: Get Pending Program Data: Retrieves all pending days in a workout program. Searches for existing workout programs by requested program ID. Returns a list of all pending days or workout sessions in the program.

Fitness: Post Program Data Capture: Adds program data into the system against a console post. If the program data already exists for the supplied program id, update the changes.

Fuel Balance Service: Retrieve the activity point balance for a user. This service is designed for experiences that need to show a user's activity point balance.

Get Activity Point Level Service: Gets the cumulative activity point level for specified time period. If no start time and end time specified the service will respond with activity points earned for a current day.

Goals—Achievements

As noted herein, users may reach achievements based on their physical activity. Achievements may be reached based on cumulative activity points, activity points for a predefined time period (e.g., less than lifetime), average activity points per time period, other metrics and the like.

Acknowledge Achievement By Achievement Id: Acknowledges that a user has seen an achievement. This service will serve as a way of indicating whether the user has triggered the 'OK/CONFIRM' on an achievement signifying that they have acknowledged the achievement. For example, once a user has acknowledged the achievement, the achievement might not be automatically displayed or provided to the user again. The user may still view or access the achievement by manually retrieving the achievement.

Acknowledge Achievement By Activity Id: Acknowledges that a user has seen all achievements associated with an activity. This service will serve as a way of indicating whether the user has triggered the 'OK/CONFIRM' on an achievement signifying that they have acknowledged the achievement.

Add Goal Resolution: Adds a goal resolution against the supplied goal id. If the goal resolution already exists for the supplied goal id, it will not add the resolution.

Copy Goal: This service is used to copy a goal for the user based on the goal associated with goalId.

Create Goal: This service is used to create a goal for the user.

Get Achievements List: Return a list of the user's achievements.

Update and Delete Goal: Update Goal: This service is used to update a goal for the user.

Delete Goal: This service is used to delete a goal for the user.

User Registration/Initiation

The below services and functions may be used to register a user to an activity monitoring system Link: Link existing user based on User Id (nuid) with an external network such as FACEBOOK or TWITTER.

Login: This service is used by applications to login a user to the activity monitoring service or system. On login, an oauth (e.g., authentication) access token is provided back to the calling application that can be used for further calls that need login enabled. External network name can be supplied to login using third-party authentication. The system may proxy these login requests to the appropriate external networks.

Pin Request for Access Token: Gets the API access token and refresh token based on the DIN (Device Identification Number) that is passed.

Pin Request for Imprint: Adds a device. This will create and return a DIN (Device Identification Number) for the device.

Pin Request for Is Logged In: Checks if the user is already logged in or not.

Pre Registration Check: Check if the supplied email address and system screen name are available for a new registration. This service is useful for any application about to register a user with the system. This service is invoked prior to registration to check if the email address, screen name/tag name, dobType and dob, and locale already available with the application can be used to register the user with the system.

Register: Register user with the supplied information. This service is used by applications to register a user with the activity system.

Token Request Service: This service might only be called by a software application to get a one-time token during the initiation/imprint flow with a DIN (Device Identification Number).

User Initiation Statistics: Returns initiation statistics if the initiation period has not ended; returns initiation result if the initiation period has ended. The initiation period may be, for example, a first 24 hours in which the user is to perform an average day's worth of activity. During the initiation period, this service will respond with the current metrics or statistics of user activity. After the initiation period, this service will respond with the final metrics or statistics accumulated during the initiation period. In a particular example, when the service is called, a start_time_local parameter is loaded, and the end time of initiation period is calculated. The end time is then checked against the current time to determine if we are still in the initiation period. If so, the values of relevant columns (e.g., requested activity metrics) are returned along with a status code 1. If the initiation period has ended, check SYNC_DATE (e.g., a date when data was last synchronized) with the end time. If SYNC_DATE is past the end time, indicating data for the initiation period is up to date and ready, the status code is set to 0. Otherwise the status code is set to 2. Additionally, the values of relevant columns are returned. Below is an example table of status codes.

| Status | Description |
| --- | --- |
| 0 | All the values are ready |
| 1 | The initiation is in progress |
| 2 | The initiation period has ended, but not all the values are ready |

Activity Service Layer

Interfaces for the activity service layer may be used to handle all login, registration and social network/community integration.

Activity List Service: Get activity List back based on the type passed in.

Create User Service: Creates a new user through the activity monitoring system or third party provider. User gets automatically logged in after registering a user successfully. During third party login, the newly-created UPM id will be fed into the third party provider. Additionally "partner" parameters can be passed in to set partner network settings to be attached to the user. This creates another network entry for a "Partner" with the network name as specified in the service call, the unique id of that user and the screen name.

If the user is passing "Partner" parameters to store for the user the following fields are required in order for the partner information to be saved. Partner data not saving might not prevent the service from continuing normally.
  partnerGuid
  partnerNetwork
  partnerScreenName Crop Profile Image of a User: Crops and uploads the profile image of a user to permanent location Delete Profile Image of a User: Deletes the profile image of a user (soft delete)

Email Content Service: This service gets the content of an email based on app, locale, type. The user sends in the number of invitation links to be created. The service implementation will get the content for a friend invitation from a specific user and a list of links (i.e specified by the count).

External Network Friend List Service: Get a list of the user's friends in an external network. Mutual friends can be excluded from the list if an additional parameter is passed in with the request.

External Network List Service: Returns the list of external networks supported by the activity monitoring service.

External Network User Check Service: This service checks to see if an external network user already exists in the system or not. This service will perform the following based on the value of action:

1. Given an external network user's unique ID, e.g., FACEBOOK user ID, the service may return an UPM ID if the user exists in the system and is linked to the external network user.

2. If there is no record found, then the service may try to match based on email provided by the caller. If there is a matching email, the service will link the external network user record with the existing UPM record with a new link type and return the upm id. Additionally the service will also setup the user to login using, e.g., FACEBOOK OAuth token or FACEBOOK credentials (email/pwd registered with FACEBOOK).

3. If the above two checks do not result in a match, create a new email only user with the information provided by the caller and link it to the external network.
  action=check→point 1 above
  action=link→points 1 and 2 above
  action=createAndLink→all of the above Friend Create Service: Sends a friend request invitation to another user, or accepts a pending one.

Friend External Create Service: Sends a friend request invitation to any external user (not a user of the activity monitoring service) via email.

Get User Security Status Service: Retrieves a user's security status based on the cookie sent and returns the user's security level. The security level is retrieved from the slCheck cookie and the AnalysisUserId cookie, depending on whether or not the user is logged in.

Get User Service: Returns core User profile data. User data is held in UPM service and this service provides a single view into user profile. It will also return the extended User profile information from social site. If this is called anonymously, a limited subset of data will be returned based on the requested user's privacy status.

Is Logged In Service: Checks if the current user is logged in and returns security level of user if user is logged in. It is necessary for a user to be logged in order to use the NSL services.

Login Service: Authenticates the user credentials to allow the user to login. A user can choose to login using their system credentials or credentials registered with any other external networks like Facebook, Twitter, etc. An activity monitoring service uses the User Profile Management (UPM) service to register and maintain a user profile. It may also use any authentication provider like Facebook, Twitter (hereafter referred to as 3PP or third party providers or external network). On successful login, it provides authorization cookies required to make subsequent calls to NSL.

An additional useful feature is "remember me". It is sent as an optional parameter in the login request. This will allow the user to be logged in until he/she explicitly signs out of the application. Currently, the duration of validity for "remember me" is set as 30 days.

Also a user may login using oAuth access token when the user is already linked to some external network. Along with their credentials, users can send partner network information and it will be stored in the database. This information is not validated by NSL. When a user passes in "Partner" parameters, the partner's network settings will be attached to the user. This in turn creates a new network entry for that "Partner" with the network name as specified in the service call.

Logout Service: Logs the user out from the NSL.

Mark as Read Notification Service: Sets a specified notification's status to 'read'.

Team Activity List Service: Get team activity List back. Team activities can be filtered based on titleId or app or both.

Upload Profile Image of a User: Uploads the profile image of a user to temporary location User Activity List Service: Get user activity List back based on the filter criteria passed in. User activities can be filtered based on titleId or app or both. This service also returns activities of any user based on the userId passed in.

User Email Check: This service checks if the email has already been used in creating an account. Since email is an unique identifier, there cannot be multiple users registered with the same email.

User External Network Link: This service will link the FB/Twitter/other external network login with the existing account. This service will also allow linking through another Social Network.

User Forgot Password: This service helps the user reset their passwords. The service will accept an email and check that a user exists with that email address and sends to that address a temporary password reset URL email. The email contains a unique one time use reset key. The user's password is not reset until the user actually uses the reset key to reset the password meaning the act of sending a password reset email alone will not reset the user's password.

User Friend Activity List Service: Get user's friends activity List back based on the filter criteria passed in. User's friend activities can be filtered based on titleId or app or both. This service also returns activities of any user's friend based on the userId passed in.

User Friend List Service: Get User Friend List along with friends basic details.

User Friends Match Service: Gets user email details (passed by the caller of the service) if that email matches/exists in the system. Mutual friends can be excluded from this list if an additional parameter is passed in with the request.

User Screen Name Check: This service checks if the screen name the user is intending to take already exists or not. Since a screen name is a unique identifier there cannot be multiple users with the same screen name.

User Search: Searches for a user based on a searchstring passed in.

User Workout Cheer List Service: This service returns all the cheers (likes and comments) posted for a user's workout from an external social network (Facebook).

User Workout Create Service: Create a user Workout. Multiple workouts can be created (maximum 10).

User Workout Finish Service: This service lets a user post a message to an external social network (ex. Facebook) indicating the finish of their Workout and their desire to have friends cheer them on.

User Workout List Service: Get the list of user workouts.

User Workout Start Service: This service lets a user post a message to an external social network (Facebook) that indicates the start of their Workout and their desire to have friends cheer them on.

Synchronization

Synchronization between an activity monitoring device, a multi-activity platform system and/or an application may be facilitated through the following APIs.

Get Server Time: Get the current GMT time of the multi-activity platform servers.

Last Date and Time Sync Service: Returns the date and time of the last sync based on the AppId (e.g., an application identifier). This service is useful for any application/device that needs to know the last time when the device synchronization occurred and know if there are new items to synchronize.

Last Sync LSO (Last Sync Offset) and LSTS (Last Sync Timestamp)—This service is used to get the last LSO (Last Sync Offset) and LSTS (Last Sync Timestamp) back as user does a sync on the device.

Last Sync Service: This service is to get the last sync details. User login and get the last sync detail by hitting the endpoint. This service is used to get the last sync delta back as user does a sync on the device.

Sync Service (Basketball): Syncs basketball user activities to an activity monitoring service back end.

Sync Service (Device X): This service is useful for any application wishing to sync user's activities between a particular device such as Device X and an activity monitoring service back end. The actual metrics being synced will have to be negotiated with the activity monitoring service for an optimal user experience.

Sync Service (Running): Syncs running user activities to an activity monitoring service back end. This service is useful for any application wishing to sync user's activities to an activity monitoring service backend. The actual metrics being synced will have to be negotiated with activity monitoring service for optimal User experience.

Sync Service (Device Y): Syncs user activities between another particular device such as Device Y to an activity monitoring service back end.

Sync Service (Training): Syncs training user activities to an activity monitoring service backend.

Sync Service (Fitness/Workouts): Syncs fitness/workout program user activities to an activity monitoring service backend.

Sync Service v2.0: Syncs user activities to an activity monitoring service back end.

Sync Status: Get the status of the recent sync activity, indicating if the back end processing is complete.

User-Oriented Information, Events and Settings

Various services and functions may be defined for defining, configuring, sharing and retrieving user profile information. Additionally, user events may be communicated using various API services. User events may include reaching activity goals, reaching various activity achievements, warnings messages, workout reminders, other alerts and the like.

Create Event Service: Send a user event to the event service. This service is useful for any application wishing to send a user event to be displayed on a user's home page or landing page of his or her account.

Delete Event Service: Send a user event to the event service. This service is useful for any application wishing to send and delete a user event to be displayed on a user's home page or landing page of his or her account.

Delete User Data: This perform a hard-delete of user data. Cache data will also be cleared. Response should be success or failure. For example, user data on any number of protocol-compliant devices including a multi-activity system, an activity monitoring device, an intermediary device and the like may be deleted in this manner.

Get and Update Privacy: Get information about the authenticated user's privacy settings. Update the authenticated user's privacy settings. Any user that uses the multi-activity platform has a profile in the multi-activity system. The GET version of this service returns the profile privacy setting associated with the authenticated user.

Get Athlete Information: Return information about an athlete.

Get Drill: Return the drill information.

Get Drill Metadata: This service will be used periodically to get drill metadata from the multi-activity system. The drill metadata is a list of prepared drills and their associated properties.

Get Friends Me Profile: Get information about the authenticated user's friend's ME profile. Any user that uses the multi-activity platform has a profile in the multi-activity system. The GET version of this service returns all the profile information associated with the authenticated user. The "Friend's" upmId should be passed through the url.

Get Insights: Get a list of insights on a user, based on a rule based system. It is possible that no insights are returned. Insights may include recommendations for the user, identification of areas for improvement, words of encouragement and the like.

Get Me Profile: Get information about the authenticated user's ME profile. Any user that uses the multi-activity platform has a profile in the multi-activity system. The GET version of this service returns all the profile information associated with the authenticated user.

Get Me Profile Basketball: Get basketball information about the authenticated user's ME profile. Any user that uses the multi-activity platform has a profile in the multi-activity system. The GET version of this service returns all the profile information associated with the authenticated user.

Get Me Profile Training: Get training information about the authenticated user's ME profile. Any user that uses the multi-activity platform has a profile in the multi-activity system. The GET version of this service returns all the profile information associated with the authenticated user.

Get Me Profile User Header: Get information about the authenticated user's Header information. The GET version of this service returns all the profile information associated with the authenticated user.

Get Mobile App Summary: Returns the user's profile data, lifetime totals, achievements, and last 30 activities for the appid given in the request header. For example, different application may be configured to consume or detect different activities. Accordingly, only those activities consumable by the application identified by the appid may be returned.

Get Multi-Activity Profile: Get information about the authenticated user's multi-activity profile. Any user that uses the multi-activity platform has a profile in multi-activity system. The GET version of this service returns all the profile information associated with the authenticated user across all verticals. If a specific mobile application (for example Basketball) is calling the multi-activity profile, then the calling application's specific records are returned in the response. In some arrangements, the sorting of the returned records must be done by the calling application.

Get Profile and Update Profile: Get information about the authenticated user's profile. Update the profile of the authenticated user. The PUT version of this service will update the profile with the provided information. If an item is included in the request body, the value of the item will be updated; if the value is null, the item will be removed. If an item is not included in the request body, it will be ignored. However, if the item is required, an error will be thrown. This service might not update a UPM database. The GET version of this service returns all the profile information associated with the authenticated user.

Get Trainers and Athletes Metadata Information: Return the list of all athletes/trainers/celebs along with their details.

Initial Assessment: Login the user into the multi-activity system.

List Athletes: Return a list of athletes.

List Drills: Returns a list of drills.

Post Athlete Information: Post athletes' information to multi-activity system back end.

Post Drill Information: Post information about a drill to the multi-activity system backend.

Update Event Service: Send a user event to the event service. This service is useful for any application wishing to send and update a user event to be displayed on the home page.

Utilities

Cache Clearing Service: Clears the specified cache.

Cache Refresh Service: Posts a request to refresh the cache with a specific entity.

Event Service: Creates/Updates/Deletes an event to the Unified Event Stream (UES).

Activity Multiplier Service: Retrieve the fuel multiplier for a given fuel source.

Get Calendar: Return list of user events & user goals to be displayed on the Calendar.

Get Notifications: This service is used to get notifications. The GET returns a list of notifications based upon the request type.

List Supported External Networks: Return a list of supported networks for login to the activity monitoring service/community. The activity monitoring service/community itself may be returned as a possible network that can be used for login. Image formats can be returned in either JPG or PNG format.

List Supported Locales: Returns a list of supported locales and corresponding age limits for login to the activity monitoring system/service. This service is useful for any application wishing to pass locale information during registration, to query and obtain the list of locales supported by the system/service and the corresponding age limits.

Manual Share: Retrieves a Manual Share record of a user.

Notification Preferences 1.0: (POST) This service is used to add the notification preferences of a user to the activity monitoring system/service. (GET) This service is used to get the notification preferences of a user.

Notification Preferences 2.0: (POST) This service is used to add the notification preferences of a user to the activity monitoring system/service. (GET) This service is used to get the notification preferences of a user.

Refresh Device Token 1.0: When an application (e.g., a mobile application) wants to use push notifications, it must call this service every time it is opened in order to keep the device token assigned by the mobile device (which can change over time) up to date on the backend.

Refresh Device Token 2.0: When an application wants to use push notifications, it must call this service every time it is opened in order to keep the device token assigned by the mobile device (which can change over time) up to date on the backend.

Remove Device Token 1.0: When a smart phone (e.g., iPhone) application turns off push notifications or unlinks the user account on the device, it must call this service to remove the record of that device token from the backend.

Remove Device Token 2.0: When a smart phone (e.g., iPhone) application turns off push notifications or unlinks the user account on the device, it must call this service to remove the record of that device token from the backend.

Server Time Request: Get the current GMT time of the multi-activity servers.

Time Zone Ids: Gets a list of valid time zone ids.

Conclusion

While many of the aspects and features described herein relate to activity, similar processes, functions, systems and the like may be applied to inactivity. For example, a monitoring device may be configured to detect inactivity and such information may also be synchronized or otherwise transmitted to a multi-activity platform and system to affect a user's activity level and profile. In some examples, inactivity may be determined by the multi-activity platform and system to determine an amount of activity points that are to be deducted as a result of the inactivity.

Additionally, while the invention has been described with respect to specific examples including presently preferred modes of carrying out the invention, those skilled in the art will appreciate that there are numerous variations and permutations of the above described systems and methods. For example, various aspects of the invention may be used in different combinations and various different subcombinations of aspects of the invention may be used together in a single system or method without departing from the invention. In one example, software and applications described herein may be embodied as computer readable instructions stored in computer readable media. Also, various elements, components, and/or steps described above may be changed, changed in order, omitted, and/or additional elements, components, and/or steps may be added without departing from this invention.

What is claimed is:

1. A method performed by an athletic tracking system comprising:
    receiving physical activity data from a plurality of activity monitoring devices, each activity monitoring device including a sensor configured to measure physical activity data of a user;
    categorizing the received physical activity data based on type of activity monitoring device and based on type of physical activity;
    storing, in a first storage area, a first portion of the physical activity data corresponding to a first type of activity monitoring device and a first type of physical activity;
    storing, in a second storage area, a second portion of the physical activity data corresponding to a second type of activity monitoring device and a second type of physical activity;
    determining, based on the first type of activity monitoring device and the first type of physical activity, a first synchronization offset configured to specify a point at which synchronization of the first portion of the physical activity data is to begin; and
    determining, based on the second type of activity monitoring device and the second type of physical activity, a second synchronization offset configured to specify a point at which synchronization of the second portion of the physical activity data is to begin;
    responsive to receiving an instruction to synchronize data, modifying the physical activity data such that the first portion of the physical activity data is modified by the first synchronization offset and the second portion of the physical activity data is modified by the second synchronization offset; and
    displaying, by a display unit, a synchronized data display including the modified physical activity data.

2. The method of claim 1, further comprising:
    storing, in a third storage area, a third portion of the physical activity data corresponding to a first type of activity monitoring device and a second type of physical activity;
    storing, in a fourth storage area, a fourth portion of the physical activity data corresponding to a second type of activity monitoring device and a first type of physical activity;
    determining, based on the first type of activity monitoring device and the second type of physical activity, a third synchronization offset configured to specify a point at which synchronization of the third portion of the physical activity data is to begin; and
    determining, based on the second type of activity monitoring device and the first type of physical activity, a fourth synchronization offset configured to specify a point at which synchronization of the fourth portion of the physical activity data is to begin,
    wherein the synchronized data display includes physical activity data from the third storage area modified by the third synchronization offset and physical activity data from the fourth storage area modified by the fourth synchronization offset.

3. The method of claim 1, further comprising:
    determining whether the modified physical activity data meets a physical activity threshold; and
    presenting a goal achievement message to the display unit upon determining that the modified physical activity data meets the physical activity threshold.

4. The method of claim 1, further comprising:
    generating a first set of metrics for the first portion of the received physical activity data; and
    generating a second set of metrics for the second portion of the received physical activity data,
    wherein the first set of metrics includes at least one activity metric not included in the second set of metrics.

5. The method of claim 1, further comprising:
    determining a first predefined set of activity tags used for the first type of activity; and
    processing the first portion of the received physical activity data to extract one or more values for the first predefined set of activity tags.

6. The method of claim 5, further comprising:
    determining a second predefined set of activity tags used for the second type of activity; and
    process the second portion of the received physical activity data to extract one or more values for the second predefined set of activity tags.

7. The method of claim 1, further comprising:
    determining a number of activity points earned by the user based on the received physical activity data; and
    categorizing the determined number of activity points based on the at least one of: type of activity monitoring device used and type of physical activity performed.

8. The method of claim 1, further comprising determining whether the user has achieved a streak of two or more consecutive goal time periods in which a corresponding activity point goal has been reached.

9. The method of claim 1, further comprising recommending at least one of a product and an athletic activity based on the received physical activity data.

10. The method of claim 1, further comprising:
    processing a challenge between a first user and a second user;
    receiving a first set of physical activity data from the first user;
    receiving a second set of physical activity data from the second user; and
    determining a winner of the challenge based on the first and second sets of physical activity data.

11. A method performed by an athletic tracking system comprising:
- receiving physical activity data from a plurality of activity monitoring devices, each activity monitoring device including a sensor configured to measure physical activity data of a user, wherein the received physical activity data includes physical activity data for a plurality of types of physical activity;
- categorizing the received physical activity data into a plurality of portions based on a type of physical activity performed and based on type of activity monitoring device, wherein a first portion of the physical activity data corresponds to a first type of activity monitoring device and a first type of physical activity, and a second portion of the physical activity data corresponds to a second type of activity monitoring device and a second type of physical activity;
- determining, based on the first type of physical activity and the first type of activity monitoring device, a first synchronization offset for the first portion of the physical activity data, the first synchronization offset specifying a point at which synchronization of the first portion of the physical activity data is to begin;
- determining, based on the second type of physical activity and the second type of activity monitoring device, a second synchronization offset for the second portion of the physical activity data, the second synchronization offset specifying a point at which synchronization of the second portion of the physical activity data is to begin;
- responsive to receiving an instruction to synchronize data, modifying the physical activity data such that the first portion of the physical activity data is modified by the first synchronization offset and the second portion of the physical activity data is modified by the second synchronization offset; and
- displaying, by a display unit, a synchronized data display including the modified physical activity data.

12. The method of claim 11, further comprising:
- determining, based on the first type of physical activity and the second type of activity monitoring device, a third synchronization offset specifying a point at which synchronization of a third portion of the physical activity data is to begin; and
- determining, based on the second type of physical activity and the first type of activity monitoring device, a fourth synchronization offset specifying a point at which synchronization of a fourth portion of the physical activity data is to begin,
- wherein the synchronized data display includes the third portion of the physical activity data modified by the third synchronization offset and the fourth portion of the physical activity data modified by the fourth synchronization offset.

13. The method of claim 11, further comprising:
- storing, in a first storage area, the first portion of the physical activity data; and
- storing, in a second storage area, the second portion of the physical activity data.

14. The method of claim 11, further comprising:
- receiving additional physical activity data; and
- updating at least one of the first synchronization offset and the second synchronization offset based on the additional physical activity data.

15. The method of claim 11, further comprising:
- determining whether the modified physical activity data meets a physical activity threshold; and
- presenting a goal achievement message to the display unit upon determining that the modified physical activity data meets the physical activity threshold.

16. A method performed by an athletic tracking system comprising:
- storing, in a first storage area, a first portion of physical activity data received from a sensor configured to measure physical activity data of a user, the first portion of physical activity data corresponding to a first type of physical activity performed;
- storing, in a second storage area, a second portion of the physical activity data received from a sensor configured to measure physical activity data of a user, the second portion of the physical activity data corresponding to a second type of physical activity performed;
- defining a first data offset for synchronizing the first portion of the physical activity data associated with a first device;
- defining a second data offset for synchronizing the first portion of the physical activity data associated with a second device;
- defining a third data offset for synchronizing the second portion of the physical activity data associated with the first device;
- defining a fourth data offset for synchronizing the second portion of the physical activity data associated with the second device;
- responsive to receiving an instruction to synchronize data with the first device, modifying the physical activity data such that the first portion of the physical activity data is modified by the first data offset and the second portion of the physical activity data is modified by the third data offset; and
- displaying, by a display unit, a synchronized data display including the modified physical activity data synchronized with the first device.

17. The method of claim 16, further comprising:
- responsive to receiving an instruction to synchronize data with the second device, modifying the physical activity data such that the first portion of the physical activity data modified by the second data offset and the second portion of the physical activity data modified by the fourth data offset; and
- displaying, by a display unit, a synchronized data display including the modified physical activity data synchronized with the second device.

18. The method of claim 16, further comprising:
- determining whether the first data offset is greater than the second data offset; and
- in response to determining that the first data offset is greater than the second data offset, updating the second data offset to equal the first data offset.

19. The method of claim 16, further comprising:
- determining that the first device has synchronized the at least a portion of the physical activity data with the second device; and
- in response to determining that the first device has synchronized the at least a portion of the physical activity data with the second device, updating the second data offset.

20. The method of claim 16, further comprising:
- providing a visualization to at least a portion of the display unit of the received physical activity data, wherein different visualizations are provided depending on the at least one of a type of activity monitoring device used and the type of physical activity performed.

\* \* \* \* \*